US012709768B2

(12) United States Patent
Markosyan et al.

(10) Patent No.: US 12,709,768 B2
(45) Date of Patent: Aug. 18, 2026

(54) HIGH-PURITY STEVIOL GLYCOSIDES

(71) Applicant: PureCircle USA Inc., Chicago, IL (US)

(72) Inventors: Avetik Markosyan, Yerevan (AM); Siddhartha Purkayastha, Chicago, IL (US); Christopher Bayer, Munich (DE); Andreas Vogel, Leipzig (DE); Sabrina Köpke, Leipzig (DE); Sebastian Bartsch, Leipzig (DE); Birgit Brucher, Leipzig (DE); Claudia Feller, Leipzig (DE); Stefan Schönert, Leipzig (DE); Mathias Salomo, Leipzig (DE); Thomas Schultchen, Leipzig (DE)

(73) Assignee: PureCircle USA Inc., Westchester, IL (US)

( * ) Notice: Subject to any disclaimer, the term of this patent is extended or adjusted under 35 U.S.C. 154(b) by 820 days.

(21) Appl. No.: 16/614,218

(22) PCT Filed: May 15, 2018

(86) PCT No.: PCT/US2018/032720

§ 371 (c)(1), (2) Date: Nov. 15, 2019

(87) PCT Pub. No.: WO2018/213279

PCT Pub. Date: Nov. 22, 2018

(65) Prior Publication Data

US 2020/0157594 A1 May 21, 2020

Related U.S. Application Data

(60) Provisional application No. 62/581,880, filed on Nov. 6, 2017, provisional application No. 62/506,357, filed on May 15, 2017.

(51) Int. Cl.

| | |
|---|---|
| ***C12P 19/56*** | (2006.01) |
| ***A23L 2/60*** | (2006.01) |
| ***A23L 27/30*** | (2016.01) |

(52) U.S. Cl.

CPC ................ *C12P 19/56* (2013.01); *A23L 2/60* (2013.01); *A23L 27/36* (2016.08); *A23V 2002/00* (2013.01)

(58) Field of Classification Search

CPC .. C12P 19/56; A23L 2/60; A23L 27/35; A23L 27/30; A23L 27/36; C07H 1/00; C07H 15/26; C12N 9/1048; C12N 9/1062; A23V 2002/00

USPC ........... 514/777, 34; 536/18.1; 426/48, 590, 426/658; 131/352

See application file for complete search history.

(56) References Cited

U.S. PATENT DOCUMENTS

| | | | | |
|---|---|---|---|---|
| 9,386,797 | B2 * | 7/2016 | Markosyan | A61K 31/704 |
| 9,752,174 | B2 * | 9/2017 | Markosyan | A24B 15/302 |
| 11,312,984 | B2 * | 4/2022 | Prakash | A24B 15/10 |
| 2013/0108718 | A1 * | 5/2013 | Chabot | A61K 36/28 205/688 |
| 2013/0171328 | A1 | 7/2013 | Kishore et al. | |
| 2014/0357588 | A1 * | 12/2014 | Markosyan | A24B 15/302 536/18.1 |
| 2016/0198748 | A1 | 7/2016 | Prakash et al. | |
| 2016/0298159 | A1 | 10/2016 | Tao et al. | |

FOREIGN PATENT DOCUMENTS

| | | | | |
|---|---|---|---|---|
| WO | WO 2013/176738 | A1 * | 11/2013 | C07H 1/06 |
| WO | WO 2014/193934 | A1 * | 12/2014 | C07H 1/06 |
| WO | 2015065650 | | 5/2015 | |
| WO | WO 2016/043926 | A1 * | 3/2016 | C07H 1/06 |
| WO | 2016054534 | A1 | 4/2016 | |
| WO | 2017024313 | | 2/2017 | |
| WO | 2017031424 | | 2/2017 | |
| WO | WO 2018/031955 | A2 * | 2/2018 | A23L 25/37 |

OTHER PUBLICATIONS

Wang, et al., "Efficient enzymatic production of rebaudioside A from stevioside", Bioscience, Biotechnology, and Biochemistry, Aug. 11, 2015, vol. 80, No. 1, pp. 67-73.

* cited by examiner

*Primary Examiner* — Scarlett Y Goon
*Assistant Examiner* — Sarah Grace Hibshman

(57) ABSTRACT

Methods of preparing highly purified steviol glycosides, particularly rebaudiosides M, D, E and I are described. The methods include utilizing enzyme preparations and recombinant microorganisms for converting various staring compositions to target steviol glycosides. The highly purified rebaudiosides are useful as non-caloric sweetener in edible and chewable compositions such as any beverages, confectioneries, bakery products, cookies, and chewing gums.

4 Claims, 1 Drawing Sheet

Specification includes a Sequence Listing.

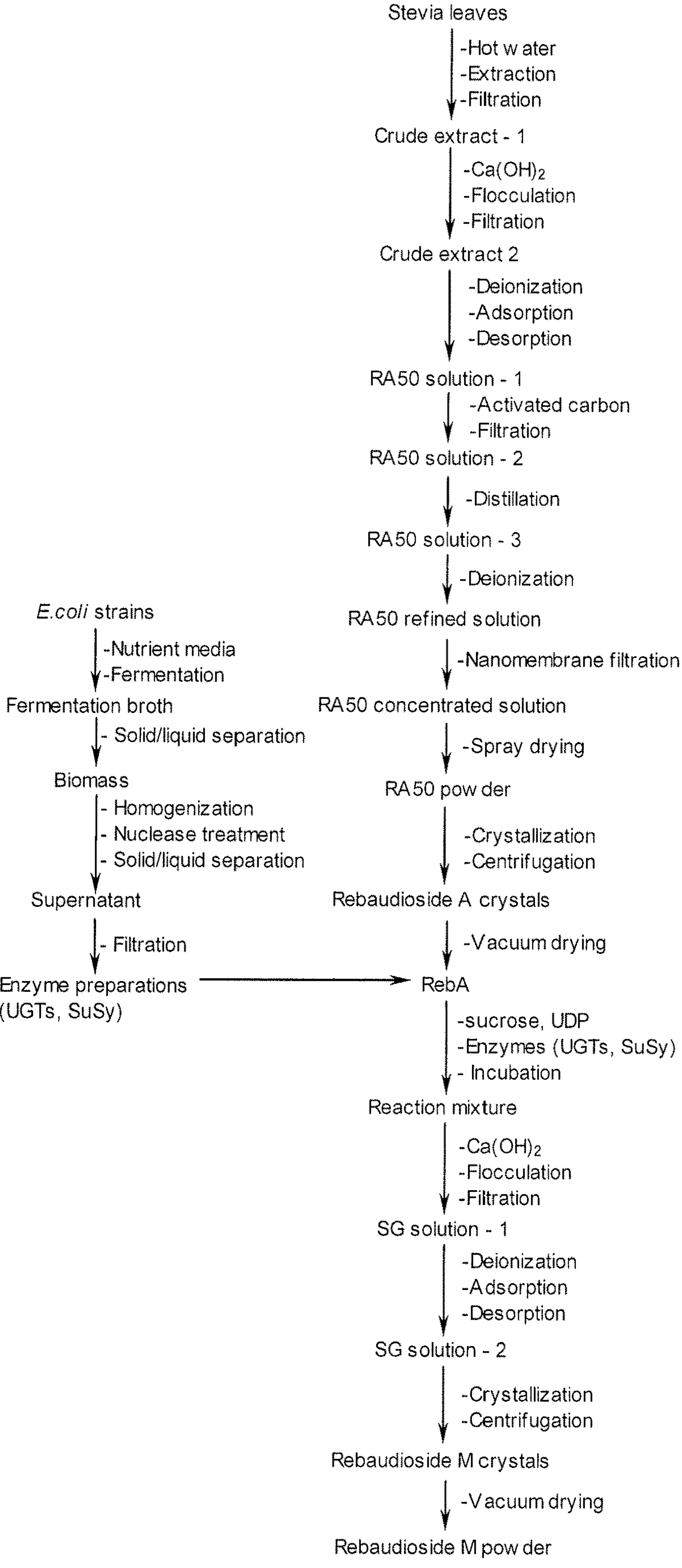
Stevia leaves
-Hot w ater
-Extraction
-Filtration
Crude extract - 1
-Ca(OH)2
-Flocculation
-Filtration
Crude extract 2
-Deionization
-Adsorption
-Desorption
RA50 solution - 1
-Activated carbon
-Filtration
RA50 solution - 2
-Distillation
RA50 solution - 3
-Deionization
RA50 refined solution
-Nanomembrane filtration
RA50 concentrated solution
-Spray drying
RA50 pow der
-Crystallization
-Centrifugation
Rebaudioside A crystals
-Vacuum drying
RebA
E.coli strains
-Nutrient media
-Fermentation
Fermentation broth
- Solid/liquid separation
Biomass
- Homogenization
- Nuclease treatment
- Solid/liquid separation
Supernatant
- Filtration
Enzyme preparations (UGTs, SuSy)
-sucrose, UDP
-Enzymes (UGTs, SuSy)
- Incubation
Reaction mixture
-Ca(OH)2
-Flocculation
-Filtration
SG solution - 1
-Deionization
-Adsorption
-Desorption
SG solution - 2
-Crystallization
-Centrifugation
Rebaudioside M crystals
-Vacuum drying
Rebaudioside M pow der

SEQUENCE LISTING

<160> NUMBER OF SEQ ID NOS: 3

<210> SEQ ID NO 1
<211> LENGTH: 808
<212> TYPE: PRT
<213> ORGANISM: Arabidopsis thaliana

<400> SEQUENCE: 1

Met Ala Asn Ala Glu Arg Met Ile Thr Arg Val His Ser Gln Arg Glu
1 5 10 15

Arg Leu Asn Glu Thr Leu Val Ser Glu Arg Asn Glu Val Leu Ala Leu
20 25 30

Leu Ser Arg Val Glu Ala Lys Gly Lys Gly Ile Leu Gln Gln Asn Gln
35 40 45

Ile Ile Ala Glu Phe Glu Ala Leu Pro Glu Gln Thr Arg Lys Lys Leu
50 55 60

Glu Gly Gly Pro Phe Phe Asp Leu Leu Lys Ser Thr Gln Glu Ala Ile
65 70 75 80

Val Leu Pro Pro Trp Val Ala Leu Ala Val Arg Pro Arg Pro Gly Val
85 90 95

Trp Glu Tyr Leu Arg Val Asn Leu His Ala Leu Val Val Glu Glu Leu
100 105 110

Gln Pro Ala Glu Phe Leu His Phe Lys Glu Glu Leu Val Asp Gly Val
115 120 125

Lys Asn Gly Asn Phe Thr Leu Glu Leu Asp Phe Glu Pro Phe Asn Ala
130 135 140

-continued

```
Ser Ile Pro Arg Pro Thr Leu His Lys Tyr Ile Gly Asn Gly Val Asp
145                 150                 155                 160

Phe Leu Asn Arg His Leu Ser Ala Lys Leu Phe His Asp Lys Glu Ser
                165                 170                 175

Leu Leu Pro Leu Leu Asp Phe Leu Arg Leu His Ser His Gln Gly Lys
            180                 185                 190

Asn Leu Met Leu Ser Glu Lys Ile Gln Asn Leu Asn Thr Leu Gln His
        195                 200                 205

Thr Leu Arg Lys Ala Glu Glu Tyr Leu Ala Glu Leu Lys Ser Glu Thr
    210                 215                 220

Leu Tyr Glu Glu Phe Glu Ala Lys Phe Glu Glu Ile Gly Leu Glu Arg
225                 230                 235                 240

Gly Trp Gly Asp Asn Ala Glu Arg Val Leu Asp Met Ile Arg Leu Leu
                245                 250                 255

Leu Asp Leu Leu Glu Ala Pro Asp Pro Ser Thr Leu Glu Thr Phe Leu
            260                 265                 270

Gly Arg Val Pro Met Val Phe Asn Val Val Ile Leu Ser Pro His Gly
        275                 280                 285

Tyr Phe Ala Gln Asp Asn Val Leu Gly Tyr Pro Asp Thr Gly Gly Gln
    290                 295                 300

Val Val Tyr Ile Leu Asp Gln Val Arg Ala Leu Glu Ile Glu Met Leu
305                 310                 315                 320

Gln Arg Ile Lys Gln Gln Gly Leu Asn Ile Lys Pro Arg Ile Leu Ile
                325                 330                 335

Leu Thr Arg Leu Leu Pro Asp Ala Val Gly Thr Thr Cys Gly Glu Arg
            340                 345                 350

Leu Glu Arg Val Tyr Asp Ser Glu Tyr Cys Asp Ile Leu Arg Val Pro
        355                 360                 365

Phe Arg Thr Glu Lys Gly Ile Val Arg Lys Trp Ile Ser Arg Phe Glu
    370                 375                 380

Val Trp Pro Tyr Leu Glu Thr Tyr Thr Glu Asp Ala Ala Val Glu Leu
385                 390                 395                 400

Ser Lys Glu Leu Asn Gly Lys Pro Asp Leu Ile Ile Gly Asn Tyr Ser
                405                 410                 415

Asp Gly Asn Leu Val Ala Ser Leu Leu Ala His Lys Leu Gly Val Thr
            420                 425                 430

Gln Cys Thr Ile Ala His Ala Leu Glu Lys Thr Lys Tyr Pro Asp Ser
        435                 440                 445

Asp Ile Tyr Trp Lys Lys Leu Asp Asp Lys Tyr His Phe Ser Cys Gln
    450                 455                 460

Phe Thr Ala Asp Ile Phe Ala Met Asn His Thr Asp Phe Ile Ile Thr
465                 470                 475                 480

Ser Thr Phe Gln Glu Ile Ala Gly Ser Lys Glu Thr Val Gly Gln Tyr
                485                 490                 495

Glu Ser His Thr Ala Phe Thr Leu Pro Gly Leu Tyr Arg Val Val His
            500                 505                 510

Gly Ile Asp Val Phe Asp Pro Lys Phe Asn Ile Val Ser Pro Gly Ala
        515                 520                 525

Asp Met Ser Ile Tyr Phe Pro Tyr Thr Glu Glu Lys Arg Arg Leu Thr
    530                 535                 540

Lys Phe His Ser Glu Ile Glu Glu Leu Leu Tyr Ser Asp Val Glu Asn
545                 550                 555                 560
```

```
Asp Glu His Leu Cys Val Leu Lys Asp Lys Lys Lys Pro Ile Leu Phe
                565                 570                 575

Thr Met Ala Arg Leu Asp Arg Val Lys Asn Leu Ser Gly Leu Val Glu
            580                 585                 590

Trp Tyr Gly Lys Asn Thr Arg Leu Arg Glu Leu Val Asn Leu Val Val
        595                 600                 605

Val Gly Gly Asp Arg Arg Lys Glu Ser Lys Asp Asn Glu Glu Lys Ala
    610                 615                 620

Glu Met Lys Lys Met Tyr Asp Leu Ile Glu Glu Tyr Lys Leu Asn Gly
625                 630                 635                 640

Gln Phe Arg Trp Ile Ser Ser Gln Met Asp Arg Val Arg Asn Gly Glu
                645                 650                 655

Leu Tyr Arg Tyr Ile Cys Asp Thr Lys Gly Ala Phe Val Gln Pro Ala
            660                 665                 670

Leu Tyr Glu Ala Phe Gly Leu Thr Val Val Glu Ala Met Thr Cys Gly
        675                 680                 685

Leu Pro Thr Phe Ala Thr Cys Lys Gly Gly Pro Ala Glu Ile Ile Val
    690                 695                 700

His Gly Lys Ser Gly Phe His Ile Asp Pro Tyr His Gly Asp Gln Ala
705                 710                 715                 720

Ala Asp Leu Leu Ala Asp Phe Phe Thr Lys Cys Lys Glu Asp Pro Ser
                725                 730                 735

His Trp Asp Glu Ile Ser Lys Gly Gly Leu Gln Arg Ile Glu Glu Lys
            740                 745                 750

Tyr Thr Trp Gln Ile Tyr Ser Gln Arg Leu Leu Thr Leu Thr Gly Val
        755                 760                 765

Tyr Gly Phe Trp Lys His Val Ser Asn Leu Asp Arg Leu Glu His Arg
    770                 775                 780

Arg Tyr Leu Glu Met Phe Tyr Ala Leu Lys Tyr Arg Pro Leu Ala Gln
785                 790                 795                 800

Ala Val Pro Leu Ala Gln Asp Asp
                805


<210> SEQ ID NO 2
<211> LENGTH: 442
<212> TYPE: PRT
<213> ORGANISM: Solanum lycopersicum

<400> SEQUENCE: 2

Met Ala Thr Asn Leu Arg Val Leu Met Phe Pro Trp Leu Ala Tyr Gly
1               5                   10                  15

His Ile Ser Pro Phe Leu Asn Ile Ala Lys Gln Leu Ala Asp Arg Gly
            20                  25                  30

Phe Leu Ile Tyr Leu Cys Ser Thr Arg Ile Asn Leu Glu Ser Ile Ile
        35                  40                  45

Lys Lys Ile Pro Glu Lys Tyr Ala Asp Ser Ile His Leu Ile Glu Leu
    50                  55                  60

Gln Leu Pro Glu Leu Pro Glu Leu Pro Pro His Tyr His Thr Thr Asn
65                  70                  75                  80

Gly Leu Pro Pro His Leu Asn Pro Thr Leu His Lys Ala Leu Lys Met
                85                  90                  95

Ser Lys Pro Asn Phe Ser Arg Ile Leu Gln Asn Leu Lys Pro Asp Leu
            100                 105                 110

Leu Ile Tyr Asp Val Leu Gln Pro Trp Ala Glu His Val Ala Asn Glu
        115                 120                 125
```

```
Gln Gly Ile Pro Ala Gly Lys Leu Leu Val Ser Cys Ala Ala Val Phe
    130                 135                 140

Ser Tyr Phe Phe Ser Phe Arg Lys Asn Pro Gly Val Glu Phe Pro Phe
145                 150                 155                 160

Pro Ala Ile His Leu Pro Glu Val Glu Lys Val Lys Ile Arg Glu Ile
                165                 170                 175

Leu Ala Lys Glu Pro Glu Glu Gly Gly Arg Leu Asp Glu Gly Asn Lys
            180                 185                 190

Gln Met Met Leu Met Cys Thr Ser Arg Thr Ile Glu Ala Lys Tyr Ile
        195                 200                 205

Asp Tyr Cys Thr Glu Leu Cys Asn Trp Lys Val Val Pro Val Gly Pro
    210                 215                 220

Pro Phe Gln Asp Leu Ile Thr Asn Asp Ala Asp Asn Lys Glu Leu Ile
225                 230                 235                 240

Asp Trp Leu Gly Thr Lys Pro Glu Asn Ser Thr Val Phe Val Ser Phe
                245                 250                 255

Gly Ser Glu Tyr Phe Leu Ser Lys Glu Asp Met Glu Glu Ile Ala Phe
            260                 265                 270

Ala Leu Glu Ala Ser Asn Val Asn Phe Ile Trp Val Val Arg Phe Pro
        275                 280                 285

Lys Gly Glu Glu Arg Asn Leu Glu Asp Ala Leu Pro Glu Gly Phe Leu
    290                 295                 300

Glu Arg Ile Gly Glu Arg Gly Arg Val Leu Asp Lys Phe Ala Pro Gln
305                 310                 315                 320

Pro Arg Ile Leu Asn His Pro Ser Thr Gly Gly Phe Ile Ser His Cys
                325                 330                 335

Gly Trp Asn Ser Val Met Glu Ser Ile Asp Phe Gly Val Pro Ile Ile
            340                 345                 350

Ala Met Pro Ile His Asn Asp Gln Pro Ile Asn Ala Lys Leu Met Val
        355                 360                 365

Glu Leu Gly Val Ala Val Glu Ile Val Arg Asp Asp Asp Gly Lys Ile
    370                 375                 380

His Arg Gly Glu Ile Ala Glu Ala Leu Lys Ser Val Val Thr Gly Glu
385                 390                 395                 400

Thr Gly Glu Ile Leu Arg Ala Lys Val Arg Glu Ile Ser Lys Asn Leu
                405                 410                 415

Lys Ser Ile Arg Asp Glu Glu Met Asp Ala Val Ala Glu Glu Leu Ile
            420                 425                 430

Gln Leu Cys Arg Asn Ser Asn Lys Ser Lys
        435                 440


<210> SEQ ID NO 3
<211> LENGTH: 458
<212> TYPE: PRT
<213> ORGANISM: Stevia rebaudiana

<400> SEQUENCE: 3

Met Glu Asn Lys Thr Glu Thr Thr Val Arg Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ala Ile Thr Ile Leu His Thr
        35                  40                  45

Asn Phe Asn Lys Pro Lys Thr Ser Asn Tyr Pro His Phe Thr Phe Arg
```

-continued

```
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Asp Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Gly Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Glu Trp Leu Asp Gln Gln Ala
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Gly Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Lys Ile Val
                325                 330                 335

Lys Trp Val Pro Gln Gln Glu Val Leu Ala His Pro Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Ser Phe Gly Gly Asp Gln Pro Leu Asn
    370                 375                 380

Ala Arg Tyr Met Ser Asp Val Leu Arg Val Gly Val Tyr Leu Glu Asn
385                 390                 395                 400

Gly Trp Glu Arg Gly Glu Val Val Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455
```

HIGH-PURITY STEVIOL GLYCOSIDES

TECHNICAL FIELD

The present invention relates to a process for preparing compositions comprising steviol glycosides, including highly purified steviol glycoside compositions.

SEQUENCE LISTING

The text file entitled "PC_71PROV_Seq_Listing_ST25.txt," created on May 15, 2017, having 15 kilobytes of data, and filed concurrently herewith, is hereby incorporated by reference in its entirety in this application.

BACKGROUND OF THE INVENTION

High intensity sweeteners possess a sweetness level that is many times greater than the sweetness level of sucrose. They are essentially non-caloric and are commonly used in diet and reduced-calorie products, including foods and beverages. High intensity sweeteners do not elicit a glycemic response, making them suitable for use in products targeted to diabetics and others interested in controlling for their intake of carbohydrates.

Steviol glycosides are a class of compounds found in the leaves of *Stevia rebaudiana* Bertoni, a perennial shrub of the Asteraceae (Compositae) family native to certain regions of South America. They are characterized structurally by a single base, steviol, differing by the presence of carbohydrate residues at positions C13 and C19. They accumulate in *Stevia* leaves, composing approximately 10%-20% of the total dry weight. On a dry weight basis, the four major glycosides found in the leaves of *Stevia* typically include stevioside (9.1%), rebaudioside A (3.8%), rebaudioside C (0.6-1.0%) and dulcoside A (0.3%). Other known steviol glycosides include rebaudioside B, C, D, E, F and M, steviolbioside and rubusoside.

Although methods are known for preparing steviol glycosides from *Stevia rebaudiana*, many of these methods are unsuitable for use commercially.

Accordingly, there remains a need for simple, efficient, and economical methods for preparing compositions comprising steviol glycosides, including highly purified steviol glycoside compositions.

SUMMARY OF THE INVENTION

The present invention provides a process for preparing a composition comprising a target steviol glycoside by contacting a starting composition comprising an organic substrate with a microbial cell and/or enzyme preparation, thereby producing a composition comprising a target steviol glycoside.

The starting composition can be any organic compound comprising at least one carbon atom. In one embodiment, the starting composition is selected from the group consisting of steviol glycosides, polyols or sugar alcohols, various carbohydrates.

The target steviol glycoside can be any steviol glycoside. In one embodiment, the target steviol glycoside is steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside M2, rebaudioside D, rebaudioside D2, rebaudioside N, rebaudioside O or a synthetic steviol glycoside.

In one embodiment, the target steviol glycoside is rebaudioside A.

In another embodiment, the target steviol glycoside is rebaudioside E.

In still another embodiment, the target steviol glycoside is rebaudioside D.

In another embodiment, the target steviol glycoside is rebaudioside I.

In yet another embodiment, the target steviol glycoside is rebaudioside M.

In some preferred embodiments enzyme preparation comprising one or more enzymes, or a microbial cell comprising one or more enzymes, capable of converting the starting composition to target steviol glycosides are used. The enzyme can be located on the surface and/or inside the cell. The enzyme preparation can be provided in the form of a whole cell suspension, a crude lysate or as purified enzyme (s). The enzyme preparation can be in free form or immobilized to a solid support made from inorganic or organic materials.

In some embodiments, a microbial cell comprises the necessary enzymes and genes encoding thereof for converting the starting composition to target steviol glycosides. Accordingly, the present invention also provides a process for preparing a composition comprising a target steviol glycoside by contacting a starting composition comprising an organic substrate with a microbial cell comprising at least one enzyme capable of converting the starting composition to target steviol glycosides, thereby producing a medium comprising at least one target steviol glycoside.

The enzymes necessary for converting the starting composition to target steviol glycosides include the steviol biosynthesis enzymes, UDP-glycosyltransferases (UGTs) and/or UDP-recycling enzyme.

In one embodiment, the steviol biosynthesis enzymes include mevalonate (MVA) pathway enzymes.

In another embodiment, the steviol biosynthesis enzymes include non-mevalonate 2-C-methyl-D-erythritol-4-phosphate pathway (MEP/DOXP) enzymes.

In one embodiment the steviol biosynthesis enzymes are selected from the group including geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), l-hydroxy-2-methyl-2(E)-butenyl 4-diphosphate synthase (HDS), 1-hydroxy-2-methyl-2(E)-butenyl 4-diphosphate reductase (HDR), acetoacetyl-CoA thiolase, truncated HMG-CoA reductase, mevalonate kinase, phosphomevalonate kinase, mevalonate pyrophosphate decarboxylase, cytochrome P450 reductase etc.

The UDP-glucosyltransferase can be any UDP-glucosyltransferase capable of adding at least one glucose unit to the steviol and or steviol glycoside substrate to provide the target steviol glycoside.

In one embodiment, steviol biosynthesis enzymes and UDP-glucosyltransferases are produced in a microbial cell. The microbial cell may be, for example, *E. coli*, *Saccharomyces* sp., *Aspergillus* sp., *Pichia* sp., *Bacillus* sp., *Yarrowia* sp. etc. In another embodiment, the UDP-glucosyltransferases are synthesized.

In one embodiment, the UDP-glucosyltransferase is selected from group including UGT74G1, UGT85C2, UGT76G1, UGT91D2 and UGTs having substantial (>85%, >86%, >87%, >88%, >89%, >90%, >91%, >92%, >93%, >94%, >95%, >96%, >97%, >98%, >99%) amino-acid sequence identity to these polypeptides as well as isolated nucleic acid molecules that code for these UGTs.

In one embodiment, steviol biosynthesis enzymes, UGTs and UDP-glucose recycling system are present in one microorganism (microbial cell). The microorganism may be for example, *E. coli, Saccharomyces* sp., *Aspergillus* sp., *Pichia* sp., *Bacillus* sp., *Yarrowia* sp.

In one embodiment, the UDP-glucosyltransferase is any UDP-glucosyltransferase capable of adding at least one glucose unit to rubusoside to form stevioside. In a particular embodiment, the UDP-glucosyltransferase is UGT91D2 or a UGT having >85% amino-acid sequence identity with UGT91D2.

In one embodiment, the UDP-glucosyltransferase is any UDP-glucosyltransferase capable of adding at least one glucose unit to stevioside to form rebaudioside A. In a particular embodiment, the UDP-glucosyltransferase is UGT76G1 or a UGT having >85% amino-acid sequence identity with UGT76G1 (SEQ ID 3).

In another embodiment, the UDP-glucosyltransferase is any UDP-glucosyltransferase capable of adding at least one glucose unit to rebaudioside A to form rebaudioside D. In a particular embodiment, the UDP-glucosyltransferase is UGT91D2 or a UGT having >85% amino-acid sequence identity with UGT91D2. In yet another embodiment the UDP-glucosyltransferase is UGTSL2 or a UGT having >85% amino-acid sequence identity with UGTSL2 (SEQ ID 2).

In yet another embodiment, the UDP-glucosyltransferase is any UDP-glucosyltransferase capable of adding at least one glucose unit to rebaudioside D to form rebaudioside M In a particular embodiment, the UDP-glucosyltransferase is UGT76G1 or a UGT having >85% amino-acid sequence identity with UGT76G1 (SEQ ID 3).

Optionally, the method of the present invention further comprises recycling UDP to provide UDP-glucose. In one embodiment, the method comprises recycling UDP by providing a recycling catalyst and a recycling substrate, such that the biotransformation of the steviol glycoside substrate to the target steviol glycoside is carried out using catalytic amounts of UDP-glucosyltransferase and UDP-glucose.

In one embodiment, the recycling catalyst is sucrose synthase. In another embodiment the sucrose synthase is SuSy_At or a sucrose synthase having >85% amino-acid sequence identity with SuSy_At (SEQ ID 1).

In one embodiment, the recycling substrate is sucrose.

Optionally, the method of the present invention further comprises separating the target steviol glycoside from the medium to provide a highly purified target steviol glycoside composition. The target steviol glycoside can be separated by at least one suitable method, such as, for example, crystallization, separation by membranes, centrifugation, extraction, chromatographic separation or a combination of such methods.

In one embodiment, the target steviol glycoside can be produced within the microorganism. In another embodiment, the target steviol glycoside can be secreted out in the medium. In one another embodiment, the released steviol glycoside can be continuously removed from the medium. In yet another embodiment, the target steviol glycoside is separated after the completion of the conversion reaction.

In one embodiment, separation produces a composition comprising greater than about 80% by weight of the target steviol glycoside on an anhydrous basis, i.e., a highly purified steviol glycoside composition. In another embodiment, separation produces a composition comprising greater than about 90% by weight of the target steviol glycoside. In particular embodiments, the composition comprises greater than about 95% by weight of the target steviol glycoside. In other embodiments, the composition comprises greater than about 99% by weight of the target steviol glycoside.

The target steviol glycoside can be in any polymorphic or amorphous form, including hydrates, solvates, anhydrous or combinations thereof.

Purified target steviol glycosides can be used in consumable products as a sweetener. Suitable consumer products include, but are not limited to, food, beverages, pharmaceutical compositions, tobacco products, nutraceutical compositions, oral hygiene compositions, and cosmetic compositions.

BRIEF DESCRIPTION OF THE DRAWINGS

FIG. 1 is a diagram showing one embodiment of the manufacturing process for steviol glycosides with a high reb M content produced by enzymatic conversion of reb A.

DETAILED DESCRIPTION

The present invention provides a process for preparing a composition comprising a target steviol glycoside by contacting a starting composition comprising an organic substrate with a microbial cell and/or enzyme preparation, thereby producing a composition comprising a target steviol glycoside.

One object of the invention is to provide an efficient biocatalytic method for preparing steviol glycosides, particularly stevioside, reb E, reb A, reb D, and reb M from various starting compositions. One particular object of the invention is to provide a manufacturing process for producing a blend of steviol glycosides having greater than about 30% reb M, hereinafter referred to as "steviol glycosides with a high reb M content".

As used herein, "biocatalysis" or "biocatalytic" refers to the use of natural or genetically engineered biocatalysts, such as enzymes, or cells comprising one or more enzyme, capable of single or multiple step chemical transformations on organic compounds. Biocatalysis processes include fermentation, biosynthesis, bioconversion and biotransformation processes. Both isolated enzyme, and whole-cell biocatalysis methods are known in the art. Biocatalyst protein enzymes can be naturally occurring or recombinant proteins.

As used herein, the term "steviol glycoside(s)" refers to a glycoside of steviol, including, but not limited to, naturally occurring steviol glycosides, e.g. steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside rebaudioside M2, rebaudioside D, rebaudioside D2, rebaudioside N, rebaudioside O, synthetic steviol glycosides, e.g. enzymatically glucosylated steviol glycosides and combinations thereof.

Starting Composition

As used herein, "starting composition" refers to any composition (generally an aqueous solution) containing one or more organic compound comprising at least one carbon atom.

In one embodiment, the starting composition is selected from the group consisting of steviol glycosides, polyols and various carbohydrates.

The starting composition steviol glycoside is selected from the group consisting of steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside M2, rebaudioside D, rebaudioside D2, rebaudioside N or rebaudioside O, or other glycoside of steviol occurring in *Stevia rebaudiana* plant and/or combinations thereof.

In one embodiment, the starting composition steviol glycoside is stevioside.

In another embodiment, the starting composition steviol glycoside is rebaudioside A. In a particular embodiment, rebaudioside A is extracted from the leaves of *Stevia rebaudiana* plants, such as *Stevia rebaudiana* Bertoni plants, and purified to greater than 95% rebaudioside A.

In still another embodiment, the starting composition steviol glycoside is rebaudioside E.

In another embodiment, the starting composition steviol glycoside is rebaudioside I.

In yet another embodiment, the starting composition steviol glycoside is rebaudioside D.

The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced.

The term "carbohydrate" refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

The starting composition may be synthetic or purified (partially or entirely), commercially available or prepared.

In one embodiment, the starting composition is glycerol.

In another embodiment, the starting composition is glucose.

In still another embodiment, the starting composition is sucrose.

In yet another embodiment, the starting composition is starch.

In another embodiment, the starting composition is maltodextrin.

The organic compound(s) of starting composition serve as a substrate(s) for the production of the target steviol glycoside(s), as described herein.

Target Steviol Glycoside

The target steviol glycoside of the present method can be any steviol glycoside that can be prepared by the process disclosed herein. In one embodiment, the target steviol glycoside is selected from the group consisting of steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside M2, rebaudioside D, rebaudioside D2, rebaudioside N or rebaudioside O, or other glycoside of steviol.

In one embodiment, the target steviol glycoside is stevioside. In another embodiment, the target steviol glycoside is rebaudioside A (reb A). In still another embodiment, the target steviol glycoside is rebaudioside E (reb E). In yet another embodiment, the target steviol glycoside is rebaudioside I (reb I). In yet another embodiment, the target steviol glycoside is rebaudioside D (reb D). In a further embodiment, the target steviol glycoside is rebaudioside M(reb M).

The target steviol glycoside can be in any polymorphic or amorphous form, including hydrates, solvates, anhydrous or combinations thereof.

In one embodiment, the present invention is a biocatalytic process for the production of reb D.

In yet another embodiment, the present invention is a biocatalytic process for the production of reb E.

In still another embodiment, the present invention is a biocatalytic process for the production of reb I.

In a further embodiment, the present invention is a biocatalytic process for the production of reb M.

Optionally, the method of the present invention further comprises separating the target steviol glycoside from the medium to provide a highly purified target steviol glycoside composition. The target steviol glycoside can be separated by any suitable method, such as, for example, crystallization, separation by membranes, centrifugation, extraction, chromatographic separation or a combination of such methods.

In particular embodiments, the process described herein results in a highly purified target steviol glycoside composition. The term "highly purified", as used herein, refers to a composition having greater than about 80% by weight of the target steviol glycoside on an anhydrous (dried) basis. In one embodiment, the highly purified target steviol glycoside composition contains greater than about 90% by weight of the target steviol glycoside on an anhydrous (dried) basis, such as, for example, greater than about 91%, greater than about 92%, greater than about 93%, greater than about 94%, greater than about 95%, greater than about 96%, greater than about 97%, greater than about 98% or greater than about 99% target steviol glycoside content on a dried basis.

In one embodiment, when the target steviol glycoside is reb M, the process described herein provides a composition having greater than about 90% reb M content by weight on a dried basis. In another particular embodiment, when the target steviol glycoside is reb M, the process described herein provides a composition comprising greater than about 95% reb M content by weight on a dried basis.

In another embodiment, when the target steviol glycoside is reb I, the process described herein provides a composition having greater than about 90% reb I content by weight on a dried basis. In another particular embodiment, when the target steviol glycoside is reb I, the process described herein provides a composition comprising greater than about 95% reb I content by weight on a dried basis.

In yet another embodiment, when the target steviol glycoside is reb D, the process described herein provides a composition greater than about 90% reb D content by weight on a dried basis. In another particular embodiment, when the target steviol glycoside is reb D, the process described herein provides a composition comprising greater than about 95% reb D content by weight on a dried basis.

In still another embodiment, when the target steviol glycoside is reb E, the process described herein provides a composition greater than about 90% reb E content by weight on a dried basis. In another particular embodiment, when the target steviol glycoside is reb E, the process described herein provides a composition comprising greater than about 95% reb E content by weight on a dried basis.

In a further embodiment, when the target steviol glycoside is reb A, the process described herein provides a composition comprising greater than about 90% reb A content by weight on a dried basis. In another particular embodiment, when the target steviol glycoside is reb A, the process described herein provides a composition comprising greater than about 95% reb A content by weight on a dried basis.

In yet a further embodiment, when the target steviol glycoside is stevioside, the process described herein provides a composition comprising greater than about 90% stevioside content by weight on a dried basis. In another particular embodiment, when the target steviol glycoside is stevioside, the process described herein provides a composition comprising greater than about 95% stevioside content by weight on a dried basis.

Microorganisms and Enzyme Preparations

In one embodiment of present invention, a microorganism (microbial cell) and/or enzyme preparation is contacted with a medium containing the starting composition to produce target steviol glycosides.

The enzyme can be provided in the form of a whole cell suspension, a crude lysate, a purified enzyme or a combination thereof. In one embodiment, the biocatalyst is a purified enzyme capable of converting the starting composition to the target steviol glycoside. In another embodiment, the biocatalyst is a crude lysate comprising at least one enzyme capable of converting the starting composition to the target steviol glycoside. In still another embodiment, the biocatalyst is a whole cell suspension comprising at least one enzyme capable of converting the starting composition to the target steviol glycoside.

In another embodiment, the biocatalyst is one or more microbial cells comprising enzyme(s) capable of converting the starting composition to the target steviol glycoside. The enzyme can be located on the surface of the cell, inside the cell or located both on the surface of the cell and inside the cell.

Suitable enzymes for converting the starting composition to target steviol glycosides include, but are not limited to, the steviol biosynthesis enzymes and UDP-glycosyltransferases (UGTs). Optionally it may include UDP recycling enzyme(s).

In one embodiment, the steviol biosynthesis enzymes include mevalonate (MVA) pathway enzymes.

In another embodiment, the steviol biosynthesis enzymes include non-mevalonate 2-C-methyl-D-erythritol-4-phosphate pathway (MEP/DOXP) enzymes.

In one embodiment, the steviol biosynthesis enzymes are selected from the group including geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS), 1-hydroxy-2-methyl-2(E)-butenyl 4-diphosphate reductase (HDR), acetoacetyl-CoA thiolase, truncated HMG-CoA reductase, mevalonate kinase, phosphomevalonate kinase, mevalonate pyrophosphate decarboxylase, cytochrome P450 reductase etc.

The UDP-glucosyltransferase can be any UDP-glucosyltransferase capable of adding at least one glucose unit to the steviol and or steviol glycoside substrate to provide the target steviol glycoside.

In one embodiment, steviol biosynthesis enzymes and UDP-glucosyltransferases are produced in a microbial cell. The microbial cell may be, for example, *E. coli*, *Saccharomyces* sp., *Aspergillus* sp., *Pichia* sp., *Bacillus* sp., *Yarrowia* sp. etc. For example, in one embodiment, the enzymes are produced by microbial fermentation of the *E. coli* production strain LE1B109 carrying the expression vector for the corresponding enzyme gene.

In another embodiment, the UDP-glucosyltransferases are synthesized.

In one embodiment, the UDP-glucosyltransferase is selected from group including UGT74G1, UGT85C2, UGT76G1, UGT91D2 and UGTs having substantial (>85%) amino-acid sequence identity to these polypeptides as well as isolated nucleic acid molecules that code for these UGTs.

In one embodiment, steviol biosynthesis enzymes, UGTs and UDP-glucose recycling system are present in one microorganism (microbial cell). The microorganism may be for example, *E. coli, Saccharomyces* sp., *Aspergillus* sp., *Pichia* sp., *Bacillus* sp., *Yarrowia* sp.

In one embodiment, the UDP-glucosyltransferase is any UDP-glucosyltransferase capable of adding at least one glucose unit to rubusoside to form stevioside. In a particular embodiment, the UDP-glucosyltransferase is UGT91D2 or a UGT having >85% amino-acid sequence identity with UGT91D2.

In one embodiment, the UDP-glucosyltransferase is any UDP-glucosyltransferase capable of adding at least one glucose unit to stevioside to form rebaudioside A. In a particular embodiment, the UDP-glucosyltransferase is UGT76G1 or a UGT having >85% amino-acid sequence identity with UGT76G1 (SEQ ID 3).

In another embodiment, the UDP-glucosyltransferase is any UDP-glucosyltransferase capable of adding at least one glucose unit to rebaudioside A to form rebaudioside D. In a particular embodiment, the UDP-glucosyltransferase is UGT91D2 or a UGT having >85% amino-acid sequence identity with UGT91D2. In yet another embodiment the UDP-glucosyltransferase is UGTSL or a UGT having >85% amino-acid sequence identity with UGTSL. In another embodiment, the UDP-glucosyltransferase is EUGT11 or a UGT having >85% amino-acid sequence identity with EUGT11. In yet another embodiment the UDP-glucosyltransferase is UGTSL2 or a UGT having >85% amino-acid sequence identity with UGTSL2 (SEQ ID 2).

In yet another embodiment, the UDP-glucosyltransferase is any UDP-glucosyltransferase capable of adding at least one glucose unit to rebaudioside D to form rebaudioside M In a particular embodiment, the UDP-glucosyltransferase is UGT76G1 or a UGT having >85% amino-acid sequence identity with UGT76G1 (SEQ ID 3).

Optionally, the method of the present invention further comprises recycling UDP to provide UDP-glucose. In one embodiment, the method comprises recycling UDP by providing a recycling catalyst and a recycling substrate, such that the biotransformation of the steviol glycoside substrate to the target steviol glycoside is carried out using catalytic amounts of UDP-glucosyltransferase and UDP-glucose. The UDP recycling enzyme can be sucrose synthase and the recycling substrate can be sucrose. In one embodiment the sucrose synthase is SuSy_At or a sucrose synthase having >85% amino-acid sequence identity with SuSy_At (SEQ ID 1).

In another embodiment, the UDP-glucosyltransferase capable of adding at least one glucose unit to starting composition steviol glycoside has >85% amino-acid sequence identity with UGTs selected from the following listing of GenInfo identifier numbers, preferably from the group presented in Table 1, and more preferably the group presented in Table 2.

| 397567 | 30680413 | 115480946 | 147798902 | 218193594 | 225443294 |
|---|---|---|---|---|---|
| 454245 | 32816174 | 116310259 | 147811764 | 218193942 | 225444853 |
| 1359905 | 32816178 | 116310985 | 147827151 | 219885307 | 225449296 |
| 1685003 | 34393978 | 116788066 | 147836230 | 222615927 | 225449700 |
| 1685005 | 37993665 | 116788606 | 147839909 | 222619587 | 225454338 |
| 2191136 | 37993671 | 116789315 | 147846163 | 222623142 | 225454340 |
| 2501497 | 37993675 | 119394507 | 147855977 | 222625633 | 225454342 |
| 2911049 | 39104603 | 119640480 | 148905778 | 222625635 | 225454473 |
| 4218003 | 41469414 | 122209731 | 148905999 | 222636620 | 225454475 |
| 4314356 | 41469452 | 125526997 | 148906835 | 222636621 | 225458362 |
| 13492674 | 42566366 | 125534279 | 148907340 | 222636628 | 225461551 |
| 13492676 | 42570280 | 125534461 | 148908935 | 222636629 | 225461556 |
| 15217773 | 42572855 | 125540090 | 148909182 | 224053242 | 225461558 |
| 15217796 | 44890129 | 125541516 | 148909920 | 224053386 | 225469538 |
| 15223396 | 46806235 | 125545408 | 148910082 | 224055535 | 225469540 |
| 15223589 | 50284482 | 125547340 | 148910154 | 224056138 | 226316457 |
| 15227766 | 51090402 | 125547520 | 148910612 | 224056160 | 226492603 |
| 15230017 | 51090594 | 125554547 | 148910769 | 224067918 | 226494221 |
| 15231757 | 52839682 | 125557592 | 156138791 | 224072747 | 226495389 |
| 15234056 | 56550539 | 125557593 | 156138797 | 224080189 | 226495945 |
| 15234195 | 62734263 | 125557608 | 156138799 | 224091845 | 226502400 |
| 15234196 | 62857204 | 125559566 | 156138803 | 224094703 | 226507980 |
| 15238503 | 62857206 | 125563266 | 165972256 | 224100653 | 226531147 |
| 15239523 | 62857210 | 125571055 | 168016721 | 224100657 | 226532094 |
| 15239525 | 62857212 | 125579728 | 171674071 | 224101569 | 238477377 |
| 15239543 | 75265643 | 125588307 | 171906258 | 224103105 | 240254512 |
| 15239937 | 75285934 | 125589492 | 183013901 | 224103633 | 242032615 |
| 15240305 | 75288884 | 125599469 | 183013903 | 224103637 | 242032621 |
| 15240534 | 77550661 | 125601477 | 186478321 | 224109218 | 242038423 |
| 15982889 | 77556148 | 126635837 | 187373030 | 224114583 | 242043290 |
| 18086351 | 82791223 | 126635845 | 187373042 | 224116284 | 242044836 |
| 18418378 | 83778990 | 126635847 | 190692175 | 224120552 | 242051252 |
| 18418380 | 89953335 | 126635863 | 194701936 | 224121288 | 242056217 |
| 18418382 | 110741436 | 126635867 | 195620060 | 224121296 | 242056219 |
| 19743740 | 110743955 | 126635883 | 209954691 | 224121300 | 242056663 |
| 19911201 | 115438196 | 126635887 | 209954719 | 224130358 | 242059339 |
| 20149064 | 115438785 | 133874210 | 209954725 | 224140703 | 242059341 |
| 20260654 | 115441237 | 133874212 | 209954733 | 224143404 | 242060922 |
| 21435782 | 115454819 | 145358033 | 210063105 | 224143406 | 242067411 |

-continued

| | | | | | |
|---|---|---|---|---|---|
| 21553613 | 115456047 | 147772508 | 210063107 | 224144306 | 242067413 |
| 21593514 | 115457492 | 147776893 | 212275846 | 224285244 | 242076258 |
| 22759895 | 115459312 | 147776894 | 216296854 | 225431707 | 242076396 |
| 23955910 | 115464719 | 147776895 | 217074506 | 225435532 | 242084750 |
| 26452040 | 115471069 | 147786916 | 218185693 | 225436321 | 242091005 |
| 28393204 | 115471071 | 147798900 | 218187075 | 225440041 | 242095206 |
| 30679796 | 115474009 | 147798901 | 218189427 | 225441116 | 242345159 |
| 242345161 | 297724601 | 326492035 | 356523945 | 357140904 | 359486938 |
| 255536859 | 297725463 | 326493430 | 356523957 | 357165849 | 359487055 |
| 255538228 | 297728331 | 326500410 | 356523959 | 357165852 | 359488135 |
| 255541676 | 297738632 | 326506816 | 356523961 | 357168415 | 359488708 |
| 255547075 | 297745347 | 326507826 | 356523963 | 357437837 | 359493630 |
| 255552620 | 297745348 | 326508394 | 356524387 | 357442755 | 359493632 |
| 255552622 | 297795735 | 326509445 | 356524403 | 357442757 | 359493634 |
| 255555343 | 297796253 | 326511261 | 356527181 | 357445729 | 359493636 |
| 255555361 | 297796257 | 326511866 | 356533209 | 357445731 | 359493815 |
| 255555363 | 297796261 | 326512412 | 356533852 | 357445733 | 359495856 |
| 255555365 | 297797587 | 326517673 | 356534718 | 357446799 | 359495858 |
| 255555369 | 297798502 | 326518800 | 356535480 | 357446805 | 359495869 |
| 255555373 | 297799226 | 326521124 | 356542996 | 357452779 | 359495871 |
| 255555377 | 297805988 | 326525567 | 356543136 | 357452781 | 359497638 |
| 255556812 | 297807499 | 326525957 | 356543932 | 357452783 | 359807261 |
| 255556818 | 297809125 | 326526607 | 356549841 | 357452787 | 374256637 |
| 255563008 | 297809127 | 326527141 | 356549843 | 357452789 | 377655465 |
| 255564074 | 297811403 | 326530093 | 356554358 | 357452791 | 378405177 |
| 255564531 | 297820040 | 326534036 | 356554360 | 357452797 | 378829085 |
| 255572878 | 297821483 | 326534312 | 356558606 | 357452799 | 387135070 |
| 255577901 | 297825217 | 332071132 | 356560333 | 357470367 | 387135072 |
| 255583249 | 297832276 | 339715876 | 356560599 | 357472193 | 387135078 |
| 255583253 | 297832280 | 342306012 | 356560749 | 357472195 | 387135092 |
| 255583255 | 297832518 | 342306016 | 356566018 | 357474295 | 387135094 |
| 255585664 | 297832520 | 343457675 | 356566169 | 357474493 | 387135098 |
| 255585666 | 297840825 | 343457677 | 356566173 | 357474497 | 387135100 |
| 255634688 | 297840827 | 350534960 | 356567761 | 357474499 | 387135134 |
| 255644801 | 297847402 | 356498085 | 356574704 | 357490035 | 387135136 |
| 255645821 | 297849372 | 356499771 | 356576401 | 357493567 | 387135174 |
| 255647456 | 300078590 | 356499777 | 356577660 | 357497139 | 387135176 |
| 255648275 | 300669727 | 356499779 | 357114993 | 357497581 | 387135184 |
| 260279126 | 302142947 | 356501328 | 357115447 | 357497671 | 387135186 |
| 260279128 | 302142948 | 356502523 | 357115451 | 357500579 | 387135188 |
| 261343326 | 302142950 | 356503180 | 357115453 | 357504663 | 387135190 |
| 283132367 | 302142951 | 356503184 | 357116080 | 357504691 | 387135192 |
| 283362112 | 302765302 | 356503295 | 357116928 | 357504699 | 387135194 |
| 289188052 | 302796334 | 356504436 | 357117461 | 357504707 | 387135282 |
| 295841350 | 302811470 | 356504523 | 357117463 | 357505859 | 387135284 |
| 296088529 | 302821107 | 356504765 | 357117829 | 357510851 | 387135294 |
| 296090415 | 302821679 | 356511113 | 357117839 | 357516975 | 387135298 |
| 296090524 | 319759260 | 356515120 | 357125059 | 359477003 | 387135300 |
| 296090526 | 319759266 | 356517088 | 357126015 | 359477998 | 387135302 |
| 297599503 | 320148814 | 356520732 | 357134488 | 359478043 | 387135304 |
| 297601531 | 326489963 | 356522586 | 357135657 | 359478286 | 387135312 |
| 297611791 | 326490273 | 356522588 | 357138503 | 359484299 | 387135314 |
| 297722841 | 326491131 | 356522590 | 357139683 | 359486936 | 387135316 |
| 387135318 | 449440433 | 460376293 | 460413408 | 462423864 | 475546199 |
| 387135320 | 449445896 | 460378310 | 460416351 | 470101924 | 475556485 |
| 387135322 | 449446454 | 460380744 | 462394387 | 470102280 | 475559699 |
| 387135324 | 449447657 | 460381726 | 462394433 | 470102858 | 475578293 |
| 387135326 | 449449002 | 460382093 | 462394557 | 470104211 | 475591753 |
| 387135328 | 449449004 | 460382095 | 462395646 | 470104264 | 475593742 |
| 388493506 | 449449006 | 460382754 | 462395678 | 470104266 | 475612072 |
| 388495496 | 449451379 | 460384935 | 462396388 | 470106317 | 475622476 |
| 388498446 | 449451589 | 460384937 | 462396389 | 470106357 | 475622507 |
| 388499220 | 449451591 | 460385076 | 462396419 | 470115448 | 475623787 |
| 388502176 | 449451593 | 460385872 | 462396542 | 470130404 | 482550481 |
| 388517521 | 449453712 | 460386018 | 462397507 | 470131550 | 482550499 |
| 388519407 | 449453714 | 460389217 | 462399998 | 470136482 | 482550740 |
| 388521413 | 449453716 | 460394872 | 462400798 | 470136484 | 482550999 |
| 388827901 | 449453732 | 460396139 | 462401217 | 470136488 | 482552352 |
| 388827903 | 449457075 | 460397862 | 462402118 | 470136492 | 482554970 |
| 388827907 | 449467555 | 460397864 | 462402237 | 470137933 | 482555336 |
| 388827909 | 449468742 | 460398541 | 462402284 | 470137937 | 482555478 |
| 388827913 | 449495638 | 460403139 | 462402416 | 470140422 | 482556454 |
| 393887637 | 449495736 | 460403141 | 462404228 | 470140426 | 482557289 |
| 393887646 | 449499880 | 460403143 | 462406358 | 470140908 | 482558462 |
| 393887649 | 449502786 | 460403145 | 462408262 | 470141232 | 482558508 |
| 393990627 | 449503471 | 460405998 | 462409325 | 470142008 | 482558547 |
| 397746860 | 449503473 | 460407578 | 462409359 | 470142010 | 482561055 |
| 397789318 | 449515857 | 460407590 | 462409777 | 470142012 | 482561555 |
| 413924864 | 449518643 | 460409128 | 462411467 | 470143607 | 482562795 |

-continued

| | | | | | |
|---|---|---|---|---|---|
| 414590349 | 449519559 | 460409134 | 462414311 | 470143939 | 482562850 |
| 414590661 | 449522783 | 460409136 | 462414416 | 470145404 | 482565074 |
| 414591157 | 449524530 | 460409459 | 462414476 | 473923244 | 482566269 |
| 414879558 | 449524591 | 460409461 | 462415526 | 474114354 | 482566296 |
| 414879559 | 449528823 | 460409463 | 462415603 | 474143634 | 482566307 |
| 414879560 | 449528825 | 460409465 | 462415731 | 474202268 | 482568689 |
| 414888074 | 449534021 | 460409467 | 462416307 | 474299266 | 482570049 |
| 431812559 | 460365546 | 460410124 | 462416920 | 474363119 | 482570572 |
| 449432064 | 460366882 | 460410126 | 462416922 | 474366157 | 482575121 |
| 449432066 | 460369823 | 460410128 | 462416923 | 474429346 | |
| 449433069 | 460369829 | 460410130 | 462416924 | 475432777 | |
| 449436944 | 460369831 | 460410132 | 462417401 | 475473002 | |
| 449438665 | 460369833 | 460410134 | 462419769 | 475489790 | |
| 449438667 | 460370755 | 460410213 | 462420317 | 475511330 | |
| 449440431 | 460374714 | 460411200 | 462423366 | 475516200 | |

TABLE 1

| GI number | Accession | Origin |
|---|---|---|
| 190692175 | ACE87855.1 | *Stevia rebaudiana* |
| 41469452 | AAS07253.1 | *Oryza saliva* |
| 62857204 | BAD95881.1 | *Ipomoea nil* |
| 62857206 | BAD95882.1 | *Ipomoea purperea* |
| 56550539 | BAD77944.1 | *Bellis perennis* |
| 115454819 | NP_001051010.1 | *Oryza sativa Japonica* Group |
| 115459312 | NP_001053256.1 | *Oryza sativa Japonica* Group |
| 115471069 | NP_001059133.1 | *Oryza saliva Japonica* Group |
| 115471071 | NP_001059134.1 | *Oryza saliva Japonica* Group |
| 116310985 | CAH67920.1 | *Oryza sativa Indica* Group |
| 116788066 | ABK24743.1 | *Picea sitchensis* |
| 122209731 | Q2V6J9.1 | *Fragaria × ananassa* |
| 125534461 | EAY81009.1 | *Oryza sativa Indica* Group |
| 125559566 | EAZ05102.1 | *Oryza sativa Indica* Group |
| 125588307 | EAZ28971.1 | *Oryza sativa Japonica* Group |
| 148907340 | ABR16806.1 | *Picea sitchensis* |
| 148910082 | ABR18123.1 | *Picea sitchensis* |
| 148910612 | ABR18376.1 | *Picea sitchensis* |
| 15234195 | NP_194486.1 | *Arabidopsis thaliana* |
| 15239523 | NP_200210.1 | *Arabidopsis thaliana* |
| 15239937 | NP_196793.1 | *Arabidopsis thaliana* |
| 1685005 | AAB36653.1 | *Nicotiana tabacum* |
| 183013903 | ACC38471.1 | *Medicago truncatula* |
| 186478321 | NP_172511.3 | *Arabidopsis thaliana* |
| 187373030 | ACD03249.1 | *Avena strigosa* |
| 194701936 | ACF85052.1 | *Zea mays* |
| 19743740 | AAL92461.1 | *Solanum lycopersicum* |
| 212275846 | NP_001131009.1 | *Zea mays* |
| 222619587 | EEE55719.1 | *Oryza sativa Japonica* Group |
| 224055535 | XP_002298527.1 | *Populus trichocarpa* |
| 224101569 | XP_002334266.1 | *Populus trichocarpa* |
| 224120552 | XP_002318358.1 | *Populus trichocarpa* |
| 224121288 | XP_002330790.1 | *Populus trichocarpa* |
| 225444853 | XP_002281094 | *Vitis vinifera* |
| 225454342 | XP_002275850.1 | *Vitis vinifera* |
| 225454475 | XP_002280923.1 | *Vitis vinifera* |
| 225461556 | XP_002285222 | *Vitis vinifera* |
| 225469540 | XP_002270294.1 | *Vitis vinifera* |
| 226495389 | NP_001148083.1 | *Zea mays* |
| 226502400 | NP_001147674.1 | *Zea mays* |
| 238477377 | ACR43489.1 | *Triticum aestivum* |
| 240254512 | NP_565540.4 | *Arabidopsis thaliana* |
| 2501497 | Q43716.1 | *Petunia × hybrida* |
| 255555369 | XP_002518721.1 | *Ricinus communis* |
| 26452040 | BAC43110.1 | *Arabidopsis thaliana* |
| 296088529 | CBI37520.3 | *Vitis vinifera* |
| 297611791 | NP_001067852.2 | *Oryza sativa Japonica* Group |
| 297795735 | XP_002865752.1 | *Arabidopsis lyrata* subsp. *lyrata* |
| 297798502 | XP_002867135.1 | *Arabidopsis lyrata* subsp. *lyrata* |
| 297820040 | XP_002877903.1 | *Arabidopsis lyrata* subsp. *lyrata* |
| 297832276 | XP_002884020.1 | *Arabidopsis lyrata* subsp. *lyrata* |
| 302821107 | XP_002992218.1 | *Selaginella moellendorffii* |
| 30680413 | NP_179446.2 | *Arabidopsis thaliana* |
| 319759266 | ADV71369.1 | *Pueraria montana* var. *lobata* |
| 326507826 | BAJ86656.1 | *Hordeum vulgare* subsp. *Vulgare* |
| 343457675 | AEM37036.1 | *Brassica rapa* subsp. *oleifera* |
| 350534960 | NP_001234680.1 | *Solanum lycopersicum* |

TABLE 1-continued

| GI number | Accession | Origin |
|---|---|---|
| 356501328 | XP_003519477.1 | *Glycine max* |
| 356522586 | XP_003529927.1 | *Glycine max* |
| 356535480 | XP_003536273.1 | *Glycine max* |
| 357445733 | XP_003593144.1 | *Medicago truncatula* |
| 357452783 | XP_003596668.1 | *Medicago truncatula* |
| 357474493 | XP_003607531.1 | *Medicago truncatula* |
| 357500579 | XP_003620578.1 | *Medicago truncatula* |
| 357504691 | XP_003622634.1 | *Medicago truncatula* |
| 359477998 | XP_003632051.1 | *Vitis vinifera* |
| 359487055 | XP_002271587 | *Vitis vinifera* |
| 359495869 | XP_003635104.1 | *Vitis vinifera* |
| 387135134 | AFJ52948.1 | *Linum usitatissimum* |
| 387135176 | AFJ52969.1 | *Linum usitatissimum* |
| 387135192 | AFJ52977.1 | *Linum usitatissimum* |
| 387135282 | AFJ53022.1 | *Linum usitatissimum* |
| 387135302 | AFJ53032.1 | *Linum usitatissimum* |
| 387135312 | AFJ53037.1 | *Linum usitatissimum* |
| 388519407 | AFK47765.1 | *Medicago truncatula* |
| 393887646 | AFN26668.1 | *Barbarea vulgaris* subsp. *arcuata* |
| 414888074 | DAA64088.1 | *Zea mays* |
| 42572855 | NP_974524.1 | *Arabidopsis thaliana* |
| 449440433 | XP_004137989.1 | *Cucumis sativus* |
| 449446454 | XP_004140986.1 | *Cucumis sativus* |
| 449449004 | XP_004142255.1 | *Cucumis sativus* |
| 449451593 | XP_004143546.1 | *Cucumis sativus* |
| 449515857 | XP_004164964.1 | *Cucumis sativus* |
| 460382095 | XP_004236775.1 | *Solanum lycopersicum* |
| 460409128 | XP_004249992.1 | *Solanum lycopersicum* |
| 460409461 | XP_004250157.1 | *Solanum lycopersicum* |
| 460409465 | XP_004250159.1 | *Solanum lycopersicum* |
| 462396388 | EMJ02187.1 | *Prunus persica* |
| 462402118 | EMJ07675.1 | *Prunus persica* |
| 462409359 | EMJ14693.1 | *Prunus persica* |
| 462416923 | EMJ21660.1 | *Prunus persica* |
| 46806235 | BAD17459.1 | *Oryza saliva Japonica* Group |
| 470104266 | XP_004288529.1 | *Fragaria vesca* subsp. *vesca* |
| 470142008 | XP_004306714.1 | *Fragaria vesca* subsp. *vesca* |
| 475432777 | EMT01232.1 | *Aegilops tauschii* |
| 51090402 | BAD35324.1 | *Oryza sativa Japonica* Group |

TABLE 2

| GI number | Accession | Origin | Internal reference |
|---|---|---|---|
| 460409128 | XP.004249992.1 | *Solanum lycopersicum* | UGTSL |
| 460386018 | XP.004238697.1 | *Solanum lycopersicum* | — |
| 460409134 | XP.004249995.1 | *Solanum lycopersicum* | — |
| 460410132 | XP.004250485.1 | *Solanum lycopersicum* | UGTSL2 |
| 460410130 | XP.004250484.1 | *Solanum lycopersicum* | — |
| 460410128 | XP.004250483.1 | *Solanum lycopersicum* | — |
| 460378310 | XP.004234916.1 | *Solanum lycopersicum* | — |
| 209954733 | BAG80557.1 | *Lycium barbarum* | UGTLB |
| 209954725 | BAG80553.1 | *Lycium barbarum* | — |

One embodiment is a microbial cell comprising an enzyme of the present invention, i.e. an enzyme capable of converting the starting composition to the target steviol glycoside. Accordingly, some embodiments of the present method include contacting a microorganism with a medium containing the starting composition to provide a medium comprising at least one target steviol glycoside.

The microorganism can be any microorganism possessing the necessary enzyme(s) for converting the starting composition to target steviol glycoside(s). These enzymes are encoded within the microorganism's genome.

Suitable microorganisms include, but are not limited to, *E. coli*, *Saccharomyces* sp., *Aspergillus* sp., *Pichia* sp., *Bacillus* sp., *Yarrowia* sp. etc.

In one embodiment, the microorganism is free when contacted with the starting composition.

In another embodiment, the microorganism is immobilized when contacted with the starting composition. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

In still another embodiment, the enzyme capable of converting the starting composition to the target steviol glycoside is secreted out of the microorganism and into the reaction medium.

The target steviol glycoside is optionally purified. Purification of the target steviol glycoside from the reaction medium can be achieved by at least one suitable method to provide a highly purified target steviol glycoside composition. Suitable methods include crystallization, separation by membranes, centrifugation, extraction (liquid or solid phase), chromatographic separation, HPLC (preparative or analytical) or a combination of such methods.

Highly purified target glycoside(s) particularly, reb M, reb D, reb I and/or reb E obtained according to this invention can be used "as-is" or in combination with other sweeteners, flavors, food ingredients and combinations thereof.

Non-limiting examples of flavors include, but are not limited to, lime, lemon, orange, fruit, banana, grape, pear, pineapple, mango, berry, bitter almond, cola, cinnamon, sugar, cotton candy, vanilla and combinations thereof.

Non-limiting examples of other food ingredients include, but are not limited to, acidulants, organic and amino acids, coloring agents, bulking agents, modified starches, gums, texturizers, preservatives, caffeine, antioxidants, emulsifiers, stabilizers, thickeners, gelling agents and combinations thereof.

Highly purified target glycoside(s) particularly, reb M, reb D, reb I and/or reb E obtained according to this invention can be prepared in various polymorphic forms, including but not limited to hydrates, solvates, anhydrous, amorphous forms and combinations thereof.

Highly purified target steviol glycoside(s), particularly, reb M, reb D, reb I and/or reb E obtained according to this invention may be incorporated as a high intensity natural sweetener in foodstuffs, beverages, pharmaceutical compositions, cosmetics, chewing gums, table top products, cereals, dairy products, toothpastes and other oral cavity compositions, etc.

Highly purified target steviol glycoside(s), particularly, reb M, reb D, reb I and/or reb E as a sweetening compound may be employed as the sole sweetener, or it may be used together with at least one naturally occurring high intensity sweeteners such as stevioside, reb A, reb B, reb C, reb F, reb N, reb O, steviolbioside, dulcoside A, rubusoside, mogrosides, brazzein, neohesperidin dihydrochalcone, glycyrrhizic acid and its salts, thaumatin, perillartine, pernandulcin, mukuroziosides, baiyunoside, phlomisoside-1, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, Luo Han Guo sweetener, mogroside V, siamenoside and combinations thereof.

In a particular embodiment, reb M, reb D, reb I and/or reb E can be used in a sweetener composition comprising a compound selected from the group consisting of reb A, reb B, reb O, NSF-02, Mogroside V, Luo Han Guo, allulose, allose, D-tagatose, erythritol and combinations thereof.

Highly purified target steviol glycoside(s), particularly, reb M, reb D, reb I and/or reb E may also be used in combination with synthetic high intensity sweeteners such as sucralose, potassium acesulfame, aspartame, alitame, saccharin, neohesperidin dihydrochalcone, cyclamate, neotame, dulcin, suosan advantame, salts thereof, and combinations thereof.

Moreover, highly purified target steviol glycoside(s), particularly, reb M, reb D, reb I and/or reb E can be used in combination with natural sweetener suppressors such as gymnemic acid, hodulcin, ziziphin, lactisole, and others. reb M, reb D, reb I and/or reb E may also be combined with various umami taste enhancers. reb M, reb D, reb I and/or reb E can be mixed with umami tasting and sweet amino acids such as glutamate, aspartic acid, glycine, alanine, threonine, proline, serine, glutamate, lysine, tryptophan and combinations thereof.

Highly purified target steviol glycoside(s), particularly, reb M, reb D, reb I and/or reb E can be used in combination with one or more additive selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

Highly purified target steviol glycoside(s), particularly, reb M, reb D, reb I and/or reb E may be combined with polyols or sugar alcohols. The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced which do not adversely affect the taste of the sweetener composition.

Highly purified target steviol glycoside(s), particularly, reb M, reb D, reb I and/or reb E may be combined with reduced calorie sweeteners such as, for example, D-tagatose, L-sugars, L-sorbose, L-arabinose and combinations thereof.

Highly purified target steviol glycoside(s), particularly, reb M, reb D, reb I and/or reb E may also be combined with various carbohydrates. The term "carbohydrate" generally refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, psicose, turanose, allose, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

Highly purified target steviol glycoside(s), particularly, reb M, reb D, reb I and/or reb E obtained according to this invention can be used in combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory. Exemplary functional ingredients are provided in WO2013/096420, the contents of which is hereby incorporated by reference.

Highly purified target steviol glycoside(s), particularly, reb M, reb D, reb I and/or reb E obtained according to this invention may be applied as a high intensity sweetener to produce zero calorie, reduced calorie or diabetic beverages and food products with improved taste characteristics. It may also be used in drinks, foodstuffs, pharmaceuticals, and other products in which sugar cannot be used. In addition, highly purified target steviol glycoside(s), particularly, reb M, reb D, reb I and/or reb E can be used as a sweetener not only for drinks, foodstuffs, and other products dedicated for human consumption, but also in animal feed and fodder with improved characteristics.

Examples of consumable products in which highly purified target steviol glycoside(s), particularly, reb M, reb D, reb I and/or reb E may be used as a sweetening compound include, but are not limited to, alcoholic beverages such as vodka, wine, beer, liquor, and sake, etc.; natural juices; refreshing drinks; carbonated soft drinks; diet drinks; zero calorie drinks; reduced calorie drinks and foods; yogurt drinks; instant juices; instant coffee; powdered types of instant beverages; canned products; syrups; fermented soybean paste; soy sauce; vinegar; dressings; mayonnaise; ketchups; curry; soup; instant bouillon; powdered soy sauce; powdered vinegar; types of biscuits; rice biscuit; crackers; bread; chocolates; caramel; candy; chewing gum; jelly; pudding; preserved fruits and vegetables; fresh cream; jam; marmalade; flower paste; powdered milk; ice cream; sorbet; vegetables and fruits packed in bottles; canned and boiled beans; meat and foods boiled in sweetened sauce; agricultural vegetable food products; seafood; ham; sausage; fish ham; fish sausage; fish paste; deep fried fish products; dried seafood products; frozen food products; preserved seaweed; preserved meat; tobacco; medicinal products; and many others. In principle it can have unlimited applications.

During the manufacturing of products such as foodstuffs, drinks, pharmaceuticals, cosmetics, table top products, and chewing gum, the conventional methods such as mixing, kneading, dissolution, pickling, permeation, percolation, sprinkling, atomizing, infusing and other methods may be used.

Moreover, the highly purified target steviol glycoside(s), reb M, reb D, reb I and/or reb E obtained in this invention may be used in dry or liquid forms.

The highly purified target steviol glycoside can be added before or after heat treatment of food products. The amount of the highly purified target steviol glycoside(s), particularly, reb M, reb D, reb I and/or reb E depends on the purpose of usage. As discussed above, it can be added alone or in combination with other compounds.

The present invention is also directed to sweetness enhancement in beverages using reb M, reb D, reb I and/or reb E. Accordingly, the present invention provides a beverage comprising a sweetener and reb M, reb D, reb I and/or reb E as a sweetness enhancer, wherein reb M, reb D, reb I and/or reb E is present in a concentration at or below their respective sweetness recognition thresholds.

As used herein, the term "sweetness enhancer" refers to a compound capable of enhancing or intensifying the perception of sweet taste in a composition, such as a beverage. The term "sweetness enhancer" is synonymous with the terms "sweet taste potentiator," "sweetness potentiator," "sweetness amplifier," and "sweetness intensifier."

The term "sweetness recognition threshold concentration," as generally used herein, is the lowest known concentration of a sweet compound that is perceivable by the human sense of taste, typically around 1.0% sucrose equivalence (1.0% SE). Generally, the sweetness enhancers may enhance or potentiate the sweet taste of sweeteners without providing any noticeable sweet taste by themselves when present at or below the sweetness recognition threshold concentration of a given sweetness enhancer; however, the sweetness enhancers may themselves provide sweet taste at concentrations above their sweetness recognition threshold concentration. The sweetness recognition threshold concentration is specific for a particular enhancer and can vary based on the beverage matrix. The sweetness recognition threshold concentration can be easily determined by taste testing increasing concentrations of a given enhancer until greater than 1.0% sucrose equivalence in a given beverage matrix is detected. The concentration that provides about 1.0% sucrose equivalence is considered the sweetness recognition threshold.

In some embodiments, sweetener is present in the beverage in an amount from about 0.5% to about 12% by weight, such as, for example, about 1.0% by weight, about 1.5% by weight, about 2.0% by weight, about 2.5% by weight, about 3.0% by weight, about 3.5% by weight, about 4.0% by weight, about 4.5% by weight, about 5.0% by weight, about 5.5% by weight, about 6.0% by weight, about 6.5% by weight, about 7.0% by weight, about 7.5% by weight, about 8.0% by weight, about 8.5% by weight, about 9.0% by weight, about 9.5% by weight, about 10.0% by weight, about 10.5% by weight, about 11.0% by weight, about 11.5% by weight or about 12.0% by weight.

In a particular embodiment, the sweetener is present in the beverage in an amount from about 0.5% of about 10%, such as for example, from about 2% to about 8%, from about 3% to about 7% or from about 4% to about 6% by weight. In a particular embodiment, the sweetener is present in the beverage in an amount from about 0.5% to about 8% by weight. In another particular embodiment, the sweetener is present in the beverage in an amount from about 2% to about 8% by weight.

In one embodiment, the sweetener is a traditional caloric sweetener. Suitable sweeteners include, but are not limited to, sucrose, fructose, glucose, high fructose corn syrup and high fructose starch syrup.

In another embodiment, the sweetener is erythritol.

In still another embodiment, the sweetener is a rare sugar. Suitable rare sugars include, but are not limited to, D-allose, D-psicose, L-ribose, D-tagatose, L-glucose, L-fucose, L-arbinose, D-turanose, D-leucrose and combinations thereof.

It is contemplated that a sweetener can be used alone, or in combination with other sweeteners.

In one embodiment, the rare sugar is D-allose. In a more particular embodiment, D-allose is present in the beverage in an amount of about 0.5% to about 10% by weight, such as, for example, from about 2% to about 8%.

In another embodiment, the rare sugar is D-psicose. In a more particular embodiment, D-psicose is present in the beverage in an amount of about 0.5% to about 10% by weight, such as, for example, from about 2% to about 8%.

In still another embodiment, the rare sugar is D-ribose. In a more particular embodiment, D-ribose is present in the beverage in an amount of about 0.5% to about 10% by weight, such as, for example, from about 2% to about 8%.

In yet another embodiment, the rare sugar is D-tagatose. In a more particular embodiment, D-tagatose is present in the beverage in an amount of about 0.5% to about 10% by weight, such as, for example, from about 2% to about 8%.

In a further embodiment, the rare sugar is L-glucose. In a more particular embodiment, L-glucose is present in the beverage in an amount of about 0.5% to about 10% by weight, such as, for example, from about 2% to about 8%.

In one embodiment, the rare sugar is L-fucose. In a more particular embodiment, L-fucose is present in the beverage in an amount of about 0.5% to about 10% by weight, such as, for example, from about 2% to about 8%.

In another embodiment, the rare sugar is L-arabinose. In a more particular embodiment, L-arabinose is present in the beverage in an amount of about 0.5% to about 10% by weight, such as, for example, from about 2% to about 8%.

In yet another embodiment, the rare sugar is D-turanose. In a more particular embodiment, D-turanose is present in the beverage in an amount of about 0.5% to about 10% by weight, such as, for example, from about 2% to about 8%.

In yet another embodiment, the rare sugar is D-leucrose. In a more particular embodiment, D-leucrose is present in the beverage in an amount of about 0.5% to about 10% by weight, such as, for example, from about 2% to about 8%.

The addition of the sweetness enhancer at a concentration at or below its sweetness recognition threshold increases the detected sucrose equivalence of the beverage comprising the sweetener and the sweetness enhancer compared to a corresponding beverage in the absence of the sweetness enhancer. Moreover, sweetness can be increased by an amount more than the detectable sweetness of a solution containing the same concentration of the at least one sweetness enhancer in the absence of any sweetener.

Accordingly, the present invention also provides a method for enhancing the sweetness of a beverage comprising a sweetener comprising providing a beverage comprising a sweetener and adding a sweetness enhancer selected from reb M, reb D, reb and/or reb E or a combination thereof, wherein reb M, reb D, reb I and/or reb E are present in a concentration at or below their sweetness recognition thresholds.

Addition of reb M, reb D, reb I and/or reb E in a concentration at or below the sweetness recognition threshold to a beverage containing a sweetener may increase the detected sucrose equivalence from about 1.0% to about 5.0%, such as, for example, about 1.0%, about 1.5%, about 2.0%, about 2.5%, about 3.0%, about 3.5%, about 4.0%, about 4.5% or about 5.0%.

The following examples illustrate preferred embodiments of the invention for the preparation of highly purified target steviol glycoside(s), particularly, reb M, reb D, reb I and/or reb E. It will be understood that the invention is not limited to the materials, proportions, conditions and procedures set forth in the examples, which are only illustrative.

Example 1

Protein Sequences of Engineered Enzymes Used in the Biocatalytic Process

```
SEQ ID 1:
>SuSy_At, variant PM1-54-2-E05 (engineered sucrose
synthase; source of WT gene: Arabidopsis thaliana)
MANAERMITRVHSQRERLNETLVSERNEVLALLSRVEAKGKGILQQNQII

AEFEALPEQTRKKLEGGPFFDLLKSTQEAIVLPPWVALAVRPRPGVWEYL

RVNLHALVVEELQPAEFLHFKEELVDGVKNGNFTLELDFEPFNASIPRPT

LHKYIGNGVDFLNRHLSAKLFHDKESLLPLLDFLRLHSHQGKNLMLSEKI

QNLNTLQHTLRKAEEYLAELKSETLYEEFEAKFEEIGLERGWGDNAERVL

DMIRLLLDLLEAPDPSTLETFLGRVPMVFNVVILSPHGYFAQDNVLGYPD

TGGQVVYILDQVRALEIEMLQRIKQQGLNIKPRILILTRLLPDAVGTTCG

ERLERVYDSEYCDILRVPFRTEKGIVRKWISRFEVWPYLETYTEDAAVEL

SKELNGKPDLIIGNYSDGNLVASLLAHKLGVTQCTIAHALEKTKYPDSDI

YWKKLDDKYHFSCQFTADIFAMNHTDFIITSTFQEIAGSKETVGQYESHT

AFTLPGLYRVVHGIDVFDPKFNIVSPGADMSIYFPYTEEKRRLTKFHSEI

EELLYSDVENDEHLCVLKDKKKPILFTMARLDRVKNLSGLVEWYGKNTRL

RELVNLVVVGGDRRKESKDNEEKAEMKKMYDLIEEYKLNGQFRWISSQMD

RVRNGELYRYICDTKGAFVQPALYEAFGLTVVEAMTCGLPTFATCKGGPA

EIIVHGKSGFHIDPYHGDQAADLLADFFTKCKEDPSHWDEISKGGLQRIE

EKYTWQIYSQRLLTLTGVYGFWKHVSNLDRLEHRRYLEMFYALKYRPLAQ

AVPLAQDD

SEQ ID 2:
>UGTS1-0234 (engineered glycosyltransferase;
UGTSL2; source of WT gene: Solanum lycopersicum)
MATNLRVLMFPWLAYGHISPFLNIAKQLADRGFLIYLCSTRINLESIIKK

IPEKYADSIHLIELQLPELPELPPHYHTTNGLPPHLNPTLHKALKMSKPN

FSRILQNLKPDLLIYDVLQPWAEHVANEQGIPAGKLLVSCAAVFSYFFSF

RKNPGVEFPFPAIHLPEVEKVKIREILAKEPEEGGRLDEGNKQMMLMCTS

RTIEAKYIDYCTELCNWKVVPVGPPFQDLITNDADNKELIDWLGTKPENS

TVFVSFGSEYFLSKEDMEEIAFALEASNVNFIWVVRFPKGEERNLEDALP

EGFLERIGERGRVLDKFAPQPRILNHPSTGGFISHCGWNSVMESIDFGVP

IIAMPIHNDQPINAKLMVELGVAVEIVRDDDGKIHRGEIAEALKSVVTGE

TGEILRAKVREISKNLKSIRDEEMDAVAEELIQLCRNSNKSK

SEQ ID 3:
>UGTSr-0042 (engineered glycosyltransferase;
UGT76G1; source of WT gene: Stevia rebaudiana)
MENKTETTVRRRRRIILFPVPFQGHINPILQLANVLYSKGFAITILHTNF

NKPKTSNYPHFTFRFILDNDPQDERISNLPTHGPLAGMRIPIINEHGADE

LRRELELLMLASEEDEEVSCLITDALWYFAQDVADSLNLRRLVLMTSSLE

NFHAHVSLPQFDELGYLDPDDKTRLEEQASGFPMLKVKDIKSAYSNWQIG

KEILGKMIKQTKASSGVIWNSFKELEESELETVIREIPAPSFLIPLPKHL

TASSSSLLDHDRTVFEWLDQQAPSSVLYVSFGSTSEVDEKDFLEIARGLV

DSGQSFLWVVRPGFVKGSTWVEPLPDGFLGERGKIVKWVPQQEVLAHPAI
```

-continued

```
GAFWTHSGWNSTLESVCEGVPMIFSSFGGDQPLNARYMSDVLRVGVYLEN

GWERGEVVNAIRRVMVDEEGEYIRQNARVLKQKADVSLMKGGSSYESLES

LVSYISSL
```

Example 2

Expression and Formulation of SuSy_At Variant of SEQ ID 1

The gene coding for the SuSy_At variant of SEQ ID 1 (EXAMPLE 1) was cloned into the expression vector pLE1A17 (derivative of pRSF-1b, Novagen). The resulting plasmid was used for transformation of *E. coli* BL21(DE3) cells.

Cells were cultivated in ZYM505 medium (F. William Studier, Protein Expression and Purification 41 (2005) 207-234) supplemented with kanamycin (50 mg/l) at 37° C. Expression of the genes was induced at logarithmic phase by IPTG (0.2 mM) and carried out at 30° C. and 200 rpm for 16-18 hours.

Cells were harvested by centrifugation (3220×g, 20 min, 4° C.) and re-suspended to an optical density of 200 (measured at 600 nm ($OD_{600}$)) with cell lysis buffer (100 mM Tris-HCl pH 7.0; 2 mM $MgCl_2$, DNA nuclease 20 U/mL, lysozyme 0.5 mg/mL). Cells were then disrupted by sonication and crude extracts were separated from cell debris by centrifugation (18000×g 40 min, 4° C.). The supernatant was sterilized by filtration through a 0.2 μm filter and diluted 50:50 with distilled water, resulting in an enzymatic active preparation.

For enzymatic active preparations of SuSy_At, activity in Units is defined as follows: 1 mU of SuSy turns over 1 nmol of sucrose into fructose in 1 minute. Reaction conditions for the assay are 30° C., 50 mM potassium phosphate buffer pH 7.0, 400 mM sucrose at to, 3 mM $MgCl_2$, and 15 mM uridin diphosphate (UDP).

Example 3

Expression and Formulation of UGTSl Variant of SEQ ID 2

The gene coding for the UGTSl variant of SEQ ID 2 (EXAMPLE 1) was cloned into the expression vector pLE1A17 (derivative of pRSF-1b, Novagen). The resulting plasmid was used for transformation of *E. coli* BL21(DE3) cells.

Cells were cultivated in ZYM505 medium (F. William Studier, Protein Expression and Purification 41 (2005) 207-234) supplemented with kanamycin (50 mg/1) at 37° C. Expression of the genes was induced at logarithmic phase by IPTG (0.1 mM) and carried out at 30° C. and 200 rpm for 16-18 hours.

Cells were harvested by centrifugation (3220×g, 20 min, 4° C.) and re-suspended to an optical density of 200 (measured at 600 nm ($OD_{600}$)) with cell lysis buffer (100 mM Tris-HCl pH 7.0; 2 mM $MgCl_2$, DNA nuclease 20 U/mL, lysozyme 0.5 mg/mL). Cells were then disrupted by sonication and crude extracts were separated from cell debris by centrifugation (18000×g 40 min, 4° C.). The supernatant was sterilized by filtration through a 0.2 μm filter and diluted 50:50 with 1 M sucrose solution, resulting in an enzymatic active preparation.

For enzymatic active preparations of UGTSl, activity in Units is defined as follows: 1 mU of UGTSl turns over 1 nmol of rebaudioside A (RebA) into rebaudioside D (RebD) in 1 minute. Reaction conditions for the assay are 30° C., 50 mM potassium phosphate buffer pH 7.0, 10 mM RebA at $t_0$, 500 mM sucrose, 3 mM $MgCl_2$, 0.25 mM uridin diphosphate (UDP) and 3 U/mL of SuSy_At.

Example 4

Expression and Formulation of UGTSr Variant of SEQ ID 3

The gene coding for the UGTSr variant of SEQ ID 3 (EXAMPLE 1) was cloned into the expression vector pLE1A17 (derivative of pRSF-1b, Novagen). The resulting plasmid was used for transformation of *E. coli* BL21(DE3) cells.

Cells were cultivated in ZYM505 medium (F. William Studier, Protein Expression and Purification 41 (2005) 207-234) supplemented with kanamycin (50 mg/l) at 37° C. Expression of the genes was induced at logarithmic phase by IPTG (0.1 mM) and carried out at 30° C. and 200 rpm for 16-18 hours.

Cells were harvested by centrifugation (3220×g, 20 min, 4° C.) and re-suspended to an optical density of 200 (measured at 600 nm ($OD_{600}$)) with cell lysis buffer (100 mM Tris-HCl pH 7.0; 2 mM $MgCl_2$, DNA nuclease 20 U/mL, lysozyme 0.5 mg/mL). Cells were then disrupted by sonication and crude extracts were separated from cell debris by centrifugation (18000×g 40 min, 4° C.). The supernatant was sterilized by filtration through a 0.2 μm filter and diluted 50:50 with 1 M sucrose solution, resulting in an enzymatic active preparation.

For enzymatic active preparations of UGTSr, activity in Units is defined as follows: 1 mU of UGTSr turns over 1 nmol of rebaudioside A (RebA) into rebaudioside I (RebI) in 1 minute. Reaction conditions for the assay are 30° C., 50 mM potassium phosphate buffer pH 7.0, 10 mM RebA at $t_0$, 500 mM sucrose, 3 mM $MgCl_2$, 0.25 mM uridin diphosphate (UDP) and 3 U/mL of SuSy_At.

Example 5

Synthesis of Rebaudioside M in a One-Pot Reaction, Adding UGTSl, SuSy_At and UGTSr at the Same Time Rebaudioside M (RebM) was synthesized directly from rebaudioside A (RebA) in a one-pot reaction, utilizing the three enzymes (see EXAMPLES 1, 2, 3 and 4): UGTSl (variant of SEQ ID 2), SuSy_At-(variant of SEQ ID 1) and UGTSr (variant of SEQ ID 3). The final reaction solution contained 20 mU/mL UGTSl, 160 mU/mL SuSy_At, 10 mU/mL UGTSr, 25 mM rebaudioside A, 0.5 mM uridin diphosphate (UDP), 1 M sucrose, 4 mM $MgCl_2$ and 50 mM potassium phosphate buffer (buffer stock prepared at pH 7.5), prepared in distilled water to a total volume of 1.6 mL. First, 186.6 μL of distilled water were mixed with 6.4 μL of 1M $MgCl_2$, 800 μl of 2 M sucrose, 16.1 μL of 50 mM UDP, 80 μL of 1 M potassium phosphate buffer (pH 7.5) and 400 μL of 100 mM rebaudioside A. To start the biotransformation, 26.4 μL of 1200 mU/mL UGTSl, 10.4 μl of 24600 mU/mL SuSy_At and 74.1 μL of 220 mU/mL UGTSr were added. The reaction was incubated at 30° C., shaking for 70 h. The content of RebM, RebA, as well as the content of rebaudiosides D (RebD) and rebaudiosides 1 and M2 (RebI/M2) at several time points was determined by HPLC.

For analysis, biotransformation samples were inactivated by mixing 100 μL of reaction solution with 10 μL 1M $H_2SO_4$, and adding 90 μL of 60% MeOH (in $H_2O$). Resulting samples were diluted a further 10-fold in 30% MeOH (in $H_2O$), centrifuged at 18×g for 10 min at 4° C., and supernatants were used as samples for HPLC injection. HPLC was carried out on a Shimadzu 20A series unit equipped with two pump units, an auto sampler, and a thermostat column compartment. Mobile phases A (10 mM $NaH_2PO_4$, pH 2.6) and B (Acetonitrile, HPLC grade) were mixed on-line in different ratios at different times. Separation started with 26% B, changed to 29% B at 7 min and returned to 26% at 12.5 min run time. Total run time were 17 min. The flow rate was 0.75 mL/min. The column used was a Phenomenex Kinetex 2.6 μM C18 100 A, 150×4.6 mm. The column temperature was maintained at 40° C. The injection volume was 5 μl Rebaudioside species were detected by UV at 210 nm.

Table 3 shows for each time point the conversion of rebA into identified rebaudioside species (percentages calculated from molarities).

TABLE 3

Biotransformation of RebA to RebM, (addition of UGTSl, SuSy_At and UGTSr at reaction start)

| | % conversion from RebA | | | | | |
|---|---|---|---|---|---|---|
| time/h | RebA | RebD | RebM | RebM2 | RebI | unknown |
| 0 | 100.0 | 0.0 | 0.0 | 0.00 | 0.0 | 0.0 |
| 6 | 69.0 | 6.1 | 12.5 | 0.00 | 9.0 | 3.4 |
| 22 | 33.5 | 4.2 | 39.4 | 0.02 | 18.8 | 4.1 |
| 32 | 21.1 | 3.2 | 49.5 | 0.05 | 21.6 | 4.5 |
| 47 | 8.3 | 1.8 | 62.3 | 0.06 | 24.7 | 2.9 |
| 71 | 1.5 | 0.5 | 66.9 | 0.16 | 25.3 | 5.6 |

Example 6

Synthesis of Rebaudioside M in a One-Pot Reaction, Adding UGTSl, SuSy_At at Reaction Start, but UGTSr Only after 22 h Rebaudioside M (RebM) was synthesized directly from rebaudioside A (RebA) in a one-pot reaction, utilizing the three enzymes (see EXAMPLES 1, 2, 3 and 4); UGTSl (variant of SEQ ID 2), SuSy_At (variant of SEQ ID 1) and UGTSr (variant of SEQ ID 3). The final reaction solution contained 20 mU/mL UGTSl, 160 mU/mL SuSy_At, 10 mU/mL UGTSr, 25 mM rebaudioside A, 0.5 mM uridin diphosphate (UDP), 1 M sucrose, 4 mM $MgCl_2$ and 50 mM potassium phosphate buffer (buffer stock prepared at pH 7.5), prepared in distilled water to a total volume of 1.6 mL. First, 186.6 μL of distilled water were mixed with 6.4 μL of 1M $MgCl_2$, 800 μL of 2 M sucrose, 16.1 μL of 50 mM UDP, 80 μL of 1 M potassium phosphate buffer (pH 7.5) and 400 μL of 100 mM rebaudioside A. To start the biotransformation, 26.4 μL of 1200 mU/mL UGTSl and 10.4 μL of 24600 mU/mL SuSy_At were added. The reaction was incubated at 30° C., shaking for 22 h. Then, 74.1 μL of 220 mU/mL UGTSr was added to the reaction, and the reaction was incubated at 30° C., shaking for another 49 h. The content of RebM, RebA, as well as the content of rebaudiosides D (RebD) and rebaudioside I and M2 (RebI/M2) at several time points was determined by HPLC.

For analysis, biotransformation samples were inactivated by mixing 100 μL of reaction solution with 10 μL 1M $H_2SO_4$, and adding 90 μL of 60% MeOH (in $H_2O$). Resulting samples were diluted a further 10-fold in 30% MeOH (in $H_2O$), centrifuged at 18×g for 10 min at 4° C., and supernatants were used as samples for HPLC injection. HPLC was carried out on a Shimadzu 20A series unit equipped with two pump units, an auto sampler, and a thermostat column compartment. Mobile phases A (10 mM $NaH_2PO_4$, pH 2.6) and B (Acetonitrile, HPLC grade) were mixed on-line in different ratios at different times. Separation started with 26% B, changed to 29% B at 7 min and returned to 26% at 12.5 min run time. Total run time were 17 min. The flow rate was 0.75 mL/min. The column used was a Phenomenex Kinetex 2.6 nm C18 100 A, 150×4.6 mm. The column temperature was maintained at 40° C. The injection volume was 5 μl Rebaudioside species were detected by UV at 210 nm.

Table 4 shows for each time point the conversion of RebA into identified rebaudioside species (percentages calculated from molarities).

TABLE 4

Biotransformation of RebA to RebM, (addition of UGTSl and SuSy_At at reaction start, addition of UGTSr after 22 h)

| time/h | % conversion from RebA | | | | | |
|---|---|---|---|---|---|---|
| | RebA | RebD | RebM | RebM2 | RebI | unknown |
| 0 | 100.0 | 0.0 | 0.0 | 0.0 | 0.0 | 0.0 |
| 6 | 71.7 | 28.4 | 0.0 | 0.03 | 0.0 | 0.1 |
| 22 | 25.2 | 65.9 | 0.0 | 0.12 | 0.0 | 8.8 |
| 32 | 15.8 | 55.9 | 22.6 | 0.20 | 1.3 | 4.3 |
| 47 | 9.3 | 32.1 | 54.9 | 0.28 | 2.0 | 1.5 |
| 71 | 0.9 | 2.2 | 90.6 | 0.36 | 2.6 | 3.4 |

Example 7

Construction of the Enzyme Production Microorganisms

The production strain LE1B109 is a genetically modified derivative strain of the laboratory strain *E. coli* K-12 W3110. The parental strain *E. coli* K-12 W3110 has been modified by site-directed recombination at different chromosomal loci to suit production purposes in terms of genetic stability, especially plasmid stability, and efficiency of expression and biotransformation. The expression of a number of proteases has been eliminated by deletion of the corresponding genes. Antibiotic-free selection of target clones has been enabled through deletion of one gene. One further gene has been deleted to prevent unwanted recombination effects. The gene coding for the T7 RNA polymerase from *E. coli* T7 phage and another gene copy of lacI, a repressor naturally present in *E. coli* K-12 W3110, have been inserted into the genome of W3110 to achieve a strong and regulated enzyme expression. Furthermore, the strain might carry certain deletions of endogenous enzyme genes connected to the degradation of biotransformation reactants in order to avoid side reactions. Insertions and deletions of chromosomal DNA are in general performed by integration of plasmid-based fragments carrying antibiotic resistance genes. After selection of the correct chromosomal mutants, resistance genes are excised and all plasmids are removed. No residual vector sequences or antibiotic resistance genes are left in the final cell.

The final production strain used for manufacturing each enzyme is created from the LE1B109 recipient strain by introducing an expression vector carrying the specific gene for one of the enzymes listed in Table 5. The plasmids used to transform the *E. coli* recipient strain are based on the well-known vector pRSF-1b (Merck KGaA, Darmstadt, Germany). The plasmids have been fully sequenced and do not carry antibiotic resistance genes or any other sequences of concern. The production strain LE1B109 has been sequenced to confirm absence of antibiotic resistance genes or any other sequences of concern.

TABLE 5

| Enzyme | Function | Source Organism |
|---|---|---|
| Sucrose synthase | Catalyzes the formation of UDP-glucose | *Arabidopsis thaliana* |
| UDP-glucosyltransferase UGT-Sr | Catalyzes the addition of glucose to steviol glycosides | *Stevia rebaudiana* |
| UDP-glucosyltransferase UGT-Sl | Catalyzes the addition of glucose to steviol glycosides | *Solanum lycopersicum* |

Example 8

Synthesis of Rebaudioside M in a One-Pot Reaction

One embodiment of the manufacturing process for steviol glycosides with a high reb M content produced by enzymatic conversion of reb A is shown in FIG. 1. The steviol glycoside purification processes utilized prior to and following the enzymatic conversion are consistent with the methodologies for the manufacture of steviol glycosides as described in the Chemical and Technical Assessment published by FAO/JECFA (FAO, 2016).

In the embodiment shown in FIG. 1, in stage 1, *S. rebaudiana* leaves are placed in hot water at 50 to 60° C. for 1 to 2 hours in continuous countercurrent extractors. The filtrate is separated using mesh screens, collected in a holding tank, and treated with flocculant (calcium hydroxide) to remove the mechanical particles, proteins, polysaccharides, and coloring agents. A plate-and-frame filter press is used to separate the resulting precipitate from the filtrate, and the filtrate is deionized by ion-exchange resins in (H+) and (OH—) form. The deionized filtrate is fed to a column system packed with macroporous adsorption resin that retains the glycosides. The column is washed with deionized water to remove impurities that did not adsorb to the resin and then the glycosides are desorbed using aqueous ethanol. The obtained glycoside solution is treated with activated carbon and the carbon is separated from the solution by plate-and-frame filter press. A standard evaporator is used to remove the ethanol, and the resulting aqueous solution is deionized again by ion-exchange resins in (H+) and (OH—) forms. The refined solution is concentrated using a nanofiltration membrane and the concentrated solution is spray dried to yield stevia extract powder containing >50% reb A (RA50). The RA50 powder is further purified by dissolving in aqueous ethanol and incubating at low temperature for several hours to allow for reb A to crystallize. The reb A crystals containing >95% reb A are separated by conventional centrifugation and dried in a rotary drum vacuum dryer at 110° C. and 10 mbar. The obtained powder is sifted through US 80 mesh stainless steel screens and passed through metal detectors to be packed in aluminum foil bags.

In stage 2 of the manufacturing process shown in FIG. 1, *E. coli* production strain LE1B109 carrying the expression vector for the corresponding enzyme is inoculated in sterilized culture medium composed of the ingredients listed in Table 6, and fermented.

TABLE 6

| Raw Material | Technological Function | Regulatory Status |
|---|---|---|
| Glucose | Fermentation Nutrient | Permitted for use in food as ingredient with no limitations apart from cGMP, 21 CFR §184.1857 |

TABLE 6-continued

| Raw Material | Technological Function | Regulatory Status |
|---|---|---|
| Isopropyl β-D-1-thiogaloctopyranoside (IPTG) | Inducer for enzyme expression | |
| Defined mineral components | Fermentation Nutrient | Permitted for use in food as food additive, food substance, ingredient, flavor enhancer, flavoring agent, processing aid or nutrient supplement, with no limitations apart from cGMP, each being selected from 21 CFR Parts §184, §172, §573, §182, §582. |
| Suitable antifoam agent | Processing aid | Listed in the FDA Sep. 11, 2003 letter to ETA as acceptable for use in enzyme manufacturing |
| Nuclease (i.e., NuCLEANase, food-grade) | Processing aid | |

The fermentation conditions are a pH of between 6 to 8 and a temperature of between 25 to 37° C. The fermentation process is continued until laboratory test data shows the desired enzyme production yield. Usually, after at least 15 hours, the fermentation is stopped. In a subsequent recovery process, the enzyme is isolated from the biomass. In a first solid/liquid separation, the biomass is separated from the culture broth by standard techniques (e.g., is centrifuged and/or filtered). The biomass is homogenized to disrupt the bacterial cells and treated with a nuclease (e.g., NuCLEANase, c-LEcta, Leipzig, Germany) to degrade the DNA/RNA nucleic acids released upon cell disruption. This is followed by solid/liquid separation steps to further remove cell debris and other insoluble matter. The cell-free supernatant is filtered to obtain the purified enzyme preparation. All raw materials used for fermentation and recovery are of food-grade quality or have been assessed to be fit for their intended use.

The obtained UGTSl, SuSy_At, and UGTSr enzyme preparation specifications are provided in Tables 7-9.

TABLE 7

UGTSl

| Specification Parameter | Specification | Manufacturing Lot SK4-14-001 | SK4-18-001 | SK4-19-001 |
|---|---|---|---|---|
| Activity | ≥7 U/mL | 9.6 | 12.0 | 9.2 |
| Total viable count | <50,000 CFU/g | <100 | <100 | <100 |
| *Salmonella* spp. | Absent in 25 g | Conforms | Conforms | Conforms |
| *E. coli* | Absent in 25 g | Conforms | Conforms | Conforms |
| Total conforms | ≤30 CFU/g | <10 | <10 | <10 |
| Antimicrobial activity | Negative | Negative | Negative | Negative |
| Lead | ≤5 mg/kg | 0.12 | 0.06 | 0.09 |
| TOS (%) | NS | 10.47 | 13.47 | 11.41 |

CFU = colony-forming unit;
NS = not specified;
TOS = total organic solids;
U = units [1 unit corresponds to the conversion of 1 μmol reb A/minute at 30° C. and pH 7.0]

TABLE 8

SuSy_At

| Specification Parameter | Specification | Manufacturing Lot PM2-34-001 | PM-39-001 | PM-40-001 |
|---|---|---|---|---|
| Activity | ≥400 U/mL | 413 | 547 | 512 |
| Total viable count | <50,000 CFU/g | <100 | <100 | <100 |
| *Salmonella* spp. | Absent in 25 g | Conforms | Conforms | Conforms |
| *Escherichia coli* | Absent in 25 g | Conforms | Conforms | Conforms |
| Total coliforms | ≤30 CFU/g | <10 | <10 | <10 |
| Antimicrobial activity | Negative | Negative | Negative | Negative |
| Lead | ≤5 mg/kg | 0.11 | 0.14 | 0.11 |
| TOS (%) | NS | 9.48 | 10.49 | 9.62 |

CFU = colony-forming unit;
NS = not specified;
TOS = total organic solids;
U = units [1 unit corresponds to the conversion of 1 μmol reb A/minute at 30° C. and pH 7.0]

TABLE 9

UGTSr

| Specification Parameter | Specification | Manufacturing Lot FAH-a-U3D1 | FAH-a-U4D1 | FA113-002 |
|---|---|---|---|---|
| Activity | ≥1 U/mL | 1.22 | 1.66 | 2.00 |
| Total viable count | <50,000 CFU/g | <100 | <100 | <100 |
| *Salmonella* spp. | Absent in 25 g | Conforms | Conforms | Conforms |
| *Escherichia coli* | Absent in 25 g | Conforms | Conforms | Conforms |
| Total coliforms | ≤30 CFU/g | <10 | <10 | <10 |
| Antimicrobial activity | Negative | Negative | Negative | Negative |
| Lead | ≤5 mg/kg | 0.08 | 0.07 | 0.08 |
| TOS (%) | NS | 10.53 | 13.61 | 14.17 |

CFU = colony-forming unit;
NS = not specified;
TOS = total organic solids;
U = units [1 unit corresponds to the conversion of 1 μmol reb A/minute at 30° C. and pH 7.0]

In stage 3, the products of stage 1 (reb A, >95%) and stage 2 (UGTSr, UGTSl, and SuSy_At enzymes) are mixed to initiate the enzymatic conversion process. First, the reb A (>95%) powder and sucrose are dissolved in reverse-osmosis water. Next, 5'-UDP-Na2 and UGTSr, UGTSl, and SuSy_At enzymes are added to formulate the reaction mixture. The reaction mixture is incubated at 40 to 50° C. for 10 to 48 hours. The use of different reaction times yields steviol glycoside mixtures with different ratios of starting glycoside reb A, intermediate glycosides such as reb D, and the primary final glycoside product reb M. The resulting reaction mixture containing a mixture of steviol glycosides, including those listed in Table 2.2-1, is heated to 80 to 100° C. and for 10 minutes to inactivate the enzymes.

In the last stage of manufacturing, the reaction mixture is treated with a flocculant (calcium hydroxide) to remove the mechanical particles, proteins, polysaccharides, and other impurities. A plate-and-frame filter press is used to separate the resulting precipitate from the filtrate, and the filtrate is deionized by ion-exchange resins in (H+) and (OH—) form. The deionized filtrate is fed to a column system packed with macroporous adsorption resin that retains the reb M and other steviol glycosides. The column is washed with deionized water to remove impurities that did not adsorb to the resin and then the glycosides are desorbed using aqueous ethanol. Next, the filtrate is maintained at low temperatures for several hours to allow reb M to crystallize. The reb M crystals containing >30% reb M are separated by conventional centrifugation and dried in a rotary drum vacuum at 110° C. and 10 mbar. The obtained powder is sifted through US 80 mesh stainless steel screens and passed through metal detectors to be packed in aluminum foil bags. The bags are placed in high-density polyethylene drums sealed with tamper evident seals.

Example 9

Product Specifications for Steviol Glycosides with a High Reb M Content Produced by Enzymatic Conversion of Reb A The physical and chemical specifications for certain embodiments of steviol glycosides with a high reb M content produced by enzymatic conversion of reb A are based on those established by JECFA for steviol glycosides following their 82nd meeting (JECFA, 2016a). The physical and chemical specifications for steviol glycosides with a high reb M content produced by enzymatic conversion are presented in Table 10. All analytical methods used to measure each specification parameter are internationally-recognized methods (e.g., United States Pharmacopeia [USP], Association of Official Analytical Chemists [AOAC], or JECFA). Total steviol glycoside content is measured using the high-performance liquid chromatography (HPLC) method described in the most recent JECFA specification monograph for steviol glycosides from *S. rebaudiana* Bertoni (JECFA, 2016a).

TABLE 10

| Specification Parameter | Steviol glycosides with a high reb M content | Current JECFA specifications for steviol glycosides (JECFA, 2016a) | Method of analysis |
|---|---|---|---|
| Appearance | White to off-white powder | White to light yellow powder | Sensory Evaluation |
| Total steviol glycosides (anhydrous basis) | ≥95% | ≥95% total steviol glycosides[a] | HPLC (JECFA, 2016a) |
| Loss on drying | ≤6.0% | ≤6% (105°, 2 h) | FAO/JECFA Vol 4[b] (p. 61) |
| pH (1% solution) | 4.5 to 7.0 | 4.5 to 7.0 | FAO/JECFA Vol 4 (p. 36-38) |
| Residual ethanol | <0.30% | ≤0.5% | USP[c] Method 467 |
| Residual methanol | <0.02% | <0.02% | USP Method 467 |
| Total ash | <1.0% | ≤1% | AOAC[d] Method 945.46 |
| Lead (as Pb) | <1.0 ppm | ≤1 ppm | AOAC Method 993.14 |
| Arsenic (as As) | <1.0 ppm | ≤1 ppm | AOAC Method 993.14 |
| Cadmium (as Cd) | <1.0 ppm | NS | AOAC Method 993.14 |
| Mercury (as Hg) | <1.0 ppm | NS | AOAC Method 993.14 |

TABLE 10-continued

| Specification Parameter | Steviol glycosides with a high reb M content | Current JECFA specifications for steviol glycosides (JECFA, 2016a) | Method of analysis |
|---|---|---|---|
| Residual protein | Not detected | NA | SDS-PAGE ® |
| Residual DNA | Not detected | NA | PCR[e] |

FCC = Food Chemicals Codex;
HPLC = high performance liquid chromatography;
NA = not applicable;
NS = not specified;
PCR = polymerase chain reaction;
SDS-PAGE = sodium dodecyl sulfate polyacrylamide gel electrophoresis;
USP = United States Pharmacopeia

[a]Where steviol glycosides "consists of a mixture of compounds containing a steviol backbone conjugated to any number or combination of the principal sugar moieties in any of the orientations occurring in the leaves of *Stevia rebaudiana* Bertoni including, glucose, rhamnose, xylose, fructose, deoxyglucose, galactose, and arabinose". (JECFA, 2016a, 2017).
[b]FAO/JECFA (2006). *Combined Compendium of Food Additive Specifications* [Online Edition], *General Specifications for Enzymes Analytical Methods*, Volume 4: *Analytical Methods, Test Procedures and Laboratory Solutions Used by and Referenced in the Food Specifications*. 1st to 65th JECFA Meetings, 1956-2005. (FAO JECFA Monographs 1). Rome, Italy: Food and Agriculture Organization of the United Nations (FAO), Joint FAO/WHO Expert Committee on Food Additives (JECFA). Available at: ftp://ftp.fao.org/docrep/fao/009/a0675e/a0675e00.pdf [Last updated (Web version): August 2011].
[c]USP (2012). United States Pharmacopeia, 35th edition & National Formulary, 30th edition [Online], Rockville (MD): U.S. Pharmacopeia (USP) Convention Inc. Available at: http://www.uspnf.com/[Subscription Only].
[d]AOAC (2005). *Official Methods of Analysis of the Association of Official Analytical Chemists*: Vols. 1&2, 18th edition (Current through Revision 1, 2006). Arlington (VA): Association of Official Analytical Chemists (AOAC).
[e]Method described in Section 3.5.4

The microbiological specification parameters listed in Table 11 have been established for steviol glycosides with a high reb M content produced by enzymatic conversion of reb A to ensure safe use in food and standard microbial tests appropriate for food ingredients are employed.

TABLE 11

| Specification Parameter | Specification | Method of Analysis |
|---|---|---|
| Total plate count | <1,000 CFU/g | AOAC[a] Method 966.23 |
| Yeast and mold (CFU/g) | Not detected | Standards Australia[b] Method 1766.2.2 |
| Total conforms (MPN/g) | Not detected | ISO 4831[c] |
| *Escherichia coli* count (MPN/g) | Not detected | ISO 7251[d] |
| *Salmonella* sp. | Absent in 25 g | ISO 6579[e] |

CFU = colony forming units;
MPN = most probable number
[a]AOAC (2005). *Official Methods of Analysis of the Association of Official Analytical Chemists*: Vols. 1&2, 18th edition (Current through Revision 1, 2006). Arlington (VA): Association of Official Analytical Chemists (AOAC).
[b]Standards Australia (1997). *Food microbiology. Method 2.2: Examination for specific organisms-Colony count of yeasts and moulds*. (Australian/New Zealand Standard AS 1766.2.2). Sydney, Australia: Standards Association of Australia/SAI Global.
[c]BSi (1991). *Methods for Microbiological examination of food and animal feeding stuffs - Part 3: Enumeration of coliforms - Most probable number technique*. (British Standard (BS)/International Organization for Standardization (ISO), BS 5763-3:1991 ISO 4831: 1991). London, Engl.: British Standards Institution (BSi).
[d]BSi (1993). Methods for Microbiological examination of food and animal feeding stuffs - Part 8: Enumeration of presumptive *Escherichia coli*. Most probable number technique. (British Standard (BS)/International Organization for Standardization (ISO), BS 5763-8: 1994 ISO 7251:1993). London, Engl.: British Standards Institution (BSi).
[e]BSi (2012). Microbiology of Food and Animal Feed. Horizontal Method for the Detection, Enumeration and Serotyping of *Salmonella*. Enumeration by a miniaturized most probable number technique. (PD CEN ISO/TS 6579-2:2012). London, Engl.: British Standards Institution (BSi). Information available at: http://shop.bsigroup.com/en/Product-Detail/?pid=000000000030255346.

Example 10

Product Analysis of Steviol Glycosides with a High Reb M Content Produced by Enzymatic Conversion of Reb A Physical and chemical analyses of 3 non-consecutive lots of steviol glycosides with a high reb M content produced by enzymatic conversion of reb A demonstrate that the manufacturing process, as described in Section 3.4.1, produces a consistent product that conforms to the defined specification parameters. The results of the batch analyses for the 3 production lots are summarized in Table 12.

TABLE 12

| Specification Parameter | Limit | Manufacturing Lot | | |
|---|---|---|---|---|
| | | BM050517 | SK-B-U2D1 | SK-B-U3D1 |
| Appearance | White to off-white powder | Conforms | Conforms | Conforms |
| Total steviol glycosides (anhydrous basis) | ≥95% | 98.88% | 97.91% | 97.20% |
| Loss on drying | ≤6.0% | 1.64% | 1.64% | 3.85% |
| pH (1% solution) | 4.5 to 7.0 | 6.32 | 5.99 | 5.89 |
| Residual ethanol | <0.30% | 0.041% | 0.134% | 0.133% |
| Residual methanol | <0.02% | ND | 0.001% | 0.001% |
| Total ash | <1.0% | 0.05% | <0.005% | 0.02 |
| Lead (as Pb) | <1.0 ppm | 0.021 ppm | 0.035 ppm | 0.038 ppm |
| Arsenic (as As) | <1.0 ppm | <0.005 ppm | <0.005 ppm | <0.005 ppm |
| Cadmium (as Cd) | <1.0 ppm | <0.005 ppm | <0.005 ppm | <0.005 ppm |
| Mercury (as Hg) | <1.0 ppm | <0.005 ppm | <0.005 ppm | <0.005 ppm |
| Residual protein | Not detected | ND | ND | ND |
| Residual DNA | Not detected | ND | ND | ND |

ND = not detected;
ppm = parts-per-million

Microbial analyses of 3 non-consecutive lots of steviol glycosides with a high reb M content produced by enzymatic conversion of reb A demonstrate that the microbiological specifications outlined in Example 9 are consistently met. A summary of the microbiological analyses is presented in Table 13.

TABLE 13

| Specification Parameter | Limit | Manufacturing Lot | | |
|---|---|---|---|---|
| | | BM050517 | SK-B-U2D1 | SK-B-U3D1 |
| Total plate count | <1,000 CFU/g | ND | ND | ND |
| Yeast and mold (CFU/g) | Not detected | ND | ND | ND |
| Total coliforms (MPN/g) | Not detected | ND | ND | ND |
| *Escherichia coli* count (MPN/g) | Not detected | ND | ND | ND |
| *Salmonella* sp. | Absent in 25 g | Absent | Absent | Absent |

CFU = colony forming units;
MPN = most probable number;
ND = not detected

The distribution of steviol glycosides in the final product is dependent upon the length of reaction time of the enzymes with starting material reb A extracted from the leaves of *S. rebaudiana*. Example data from 2 production lots (SK BU2D1, SK-BU3D1) presented in Table 13 demonstrates that as the enzyme reaction time proceeds from 10 to 40 hours the steviol glycoside distribution changes, with increasing amounts of reb M being produced as the reaction proceeds. Example intermediate glycosides include rebaudiosides D and I, as reported in Table 14.

TABLE 14

| Steviol Glycoside (%) | Time (hours) 0 | 14 | 16 | 18 | 21 | 40 |
|---|---|---|---|---|---|---|
| Lot SK-BU2D1 | | | | | | |
| Rebaudioside A | 100 | 30.4 | 25.6 | NM | 14.2 | 2.1 |
| Rebaudioside D | ND | 69.2 | 74.1 | NM | 43.6 | 1.7 |
| Rebaudioside I | ND | 0 | 0.1 | NM | 3.4 | 6.6 |
| Rebaudioside M2 | ND | 0.38 | 0.12 | NM | 0.14 | 0.19 |
| Rebaudioside M | ND | ND | ND | NM | 38.6 | 89.4 |
| Total Steviol Glycosides (%) | 100 | 99.98 | 99.92 | NA | 99.94 | 99.99 |
| Lot SK-BU3D1 | | | | | | |
| Rebaudioside A | 100 | NM | 28.6 | 21.1 | 9.4 | 1.2 |
| Rebaudioside D | ND | NM | 71.1 | 77.3 | 60.0 | 1.8 |
| Rebaudioside I | ND | NM | ND | 0.3 | 3.1 | 4.2 |
| Rebaudioside M2 | ND | NM | 0.28 | 0.35 | 0.34 | 0.37 |
| Rebaudioside M | ND | NM | ND | 0.9 | 27.1 | 92.5 |
| Total Steviol Glycosides (%) | 100 | NA | 99.98 | 99.95 | 99.94 | 100.1 |

NA = not applicable; ND = not detected; NM = not measured

Pursuant to the defined product specifications in Table 9 for steviol glycosides with a high reb M content produced by enzymatic conversion of reb A, the final product contains ≥95% steviol glycosides, comprised of >30% reb M and other steviol glycosides such as those listed in Table 15. The steviol glycoside distribution, measured by HPLC, is provided for 3 non-consecutive lots of final product manufactured with a 40-hour enzyme reaction time is shown in Table 16 and demonstrates that the manufacturing process produces a product with a consistent steviol glycoside distribution and that the total steviol glycosides measured is consistently ≥95%.

TABLE 15

| Common name | Trivial formula | Mol. Wt. | $R_1$ | $R_2$ |
|---|---|---|---|---|
| Rebaudioside A | SvG4 | 967 | Glcβ1- | Glcβ(1-2)[Glcβ(1-3)]Glcβ1- |
| Rebaudioside D | SvG5 | 1,129 | Glcβ(1-2)Glcβ1- | Glcβ(1-2)[Glcβ(1-3)]Glcβ1- |
| Rebaudioside I | SvG5 | 1,129 | Glcβ(1-3)Glcβ1- | Glcβ(1-2)[Glcβ(1-3)]Glcβ1- |
| Rebaudioside M | SvG6 | 1,291 | Glcβ(1-2)[Glcβ (1-3)]Glcβ1- | Glcβ(1-2)[Glcβ(1-3)]Glcβ1- |
| Rebaudioside M2 | SvG6 | 1,291 | Glcβ(1-2)[Glcβ (1-6)]Glcβ1- | Glcβ(1-2)[Glcβ(1-3)]Glcβ1- |

TABLE 16

| Steviol | Manufacturing Lot | | | |
|---|---|---|---|---|
| Glycoside (%) | BM050517 | SK-BU2D1 | SK-BU3D1 | Average |
| Rebaudioside D | 1.78[a] | 0.23 | 0.41 | 0.81 |
| Rebaudioside M | 95.98 | 95.71 | 95.43 | 95.71 |
| Rebaudioside I | 0.91 | 1.54 | 0.93 | 1.13 |
| Rebaudioside A | 0.09 | 0.28 | 0.12 | 0.16 |
| Total Steviol Glycosides (%) | 98.76 | 97.76 | 96.89 | 97.80 |

[a]Average of 3 duplicates is reported

To confirm the success of the purification techniques and confirm the absence of proteins in steviol glycosides with a high reb M content produced by enzymatic conversion of reb A, the final product is analyzed by sodium dodecyl sulfate polyacrylamide gel electrophoresis (SDS-PAGE). Samples of steviol glycosides with a high reb M content are dissolved to a concentration of 1,000 ppm, and about 10 μL from each dissolved sample is stained with 3× protein loading dye and loaded onto a precast polyacrylamide gel (10% Mini-PROTEAN® TGX™ Precast Protein Gels, BIO-RAD). Electrophoresis is conducted at 60 minutes at 130 V and the gel is stained with 0.1% Coomassie Blue R250 in 10% acetic acid, 50% methanol, and 40% water for 1 hour. Gels are destained by soaking for 4 hours in a mixture of 10% acetic acid, 50% methanol, and 40% water. If protein is present in the sample, it will be visually detected on the gel (limit of detection=0.1 μg protein). No visible protein bands were detected in any batches of final product.

To confirm the absence of residual DNA in steviol glycosides with a high reb M content produced by enzymatic conversion of reb A, a polymerase chain reaction (PCR) method was developed and primers were designed to amplify the gene of interest. Genomic DNA is extracted using a DNA extraction kit according to manufacturer's protocol. The genomic DNA is quantified using a spectrophotometer and the extracted genomic DNA is evaluated for the presence of the gene of interest. The thermal profile used is 2 minutes at 95° C. followed by 40 cycles of 10 seconds at 95° C., 30 seconds at 57° C., and 30 seconds at 72° C. Results of the PCR analysis did not detect any PCR products in any of the batches of final product (limit of detection=0.00002 ng DNA).

We claim:

1. A method for producing rebaudioside M comprising the steps of:

a. providing a starting composition comprising rebaudioside A;

b. providing an enzyme preparation or microorganism containing the enzymes: UGTSr of SEQ ID NO: 3 or a mutant variant thereof having >98% amino-acid sequence identity, and SuSy_At of SEQ ID NO: 1 and UGTS1 of SEQ ID NO: 2;

c. contacting the enzyme preparation or microorganism with a medium containing the starting composition to produce a medium comprising at least rebaudioside M.

2. The method of claim 1 further comprising the step of:

d. separating the rebaudioside M from the medium to provide a highly purified rebaudioside M.

3. The method of claim 2, wherein the rebaudioside M content is greater than 95% by weight on a dry basis.

4. The method of claim 1, wherein the microorganism is selected from the group consisting of *E. coli, Saccharomyces* sp., *Aspergillus* sp., *Pichia* sp., *Bacillus* sp., and *Yarrowia* sp.

* * * * *